United States Patent [19]
Hong et al.

[11] Patent Number: 6,060,612
[45] Date of Patent: May 9, 2000

[54] CERAMIDE-LIKE COMPOUNDS AND A METHOD FOR PREPARATION THEREOF, AND A COSMETIC COMPOSITION CONTAINING THE SAME

[75] Inventors: Jong Eon Hong; Myeung Su Ku, both of Seoul; Bo Sub Lee; Young Hun Byon, both of Yongin; Duk Hee Kim; Sang Rhin Lee, both of Seoul; Ok Sob Lee, Anyang; Hae Kwang Lee, Seoul; Jong Ho Park, Seoul; Ki Wha Lee, Seoul; Ki Tack Nam, Seoul; Jong Il Kim, Anyang; Hyun Jun Kim, Seongnam; Hey Jin Jung, Suwon, all of Rep. of Korea

[73] Assignee: Pacific Corporation, Seoul, Rep. of Korea

[21] Appl. No.: 08/988,713

[22] Filed: Dec. 10, 1997

[30] Foreign Application Priority Data

| Dec. 26, 1996 | [KR] | Rep. of Korea | 96-72388 |
| Dec. 26, 1996 | [KR] | Rep. of Korea | 96-72389 |
| Dec. 26, 1996 | [KR] | Rep. of Korea | 96-72390 |
| Dec. 27, 1996 | [KR] | Rep. of Korea | 96-73859 |
| Jul. 15, 1997 | [KR] | Rep. of Korea | 97-32804 |
| Jul. 23, 1997 | [KR] | Rep. of Korea | 97-34530 |

[51] Int. Cl.$^7$ .................. C07C 233/00; C07C 231/00
[52] U.S. Cl. .................. 554/61; 554/63; 554/64; 554/56; 554/68; 554/69; 554/66
[58] Field of Search .................. 554/66, 68, 69, 554/61, 63, 64, 65, 56

[56] References Cited

U.S. PATENT DOCUMENTS 5,198,210  3/1993  Critchley et al. .................. 424/78.03

OTHER PUBLICATIONS

Chem. abstr 94:83634, 1981.
Chem. abstr. 88:74379, 1978.
Chem. abstr. 111:102700, 1989.
Chem. abstr. 110:218786, 1989.
Chem. abstr. 122:196561, 1995.
Chem . abstr of JP08295657, 1996.
Chem. abstr of GB2230022, 1990.
R.D. Petersen, "Ceramides Key Components for Skin Protection", Cosmetics & Toiletries, vol. 107, Feb. 1992, pp. 46–49.

*Primary Examiner*—Deborah Carr
*Attorney, Agent, or Firm*—Foley & Lardner

[57] ABSTRACT

Disclosed herein is a ceramide-like compound having properties of the natural ceramides, and a method for producing the same, and a cosmetic composition containing the same as a active ingredient.

44 Claims, No Drawings

CERAMIDE-LIKE COMPOUNDS AND A METHOD FOR PREPARATION THEREOF, AND A COSMETIC COMPOSITION CONTAINING THE SAME

BACKGROUND OF THE INVENTION

1. Field of the Invention

The present invention relates to a ceramide-like compound having properties of the natural ceramides, and to a method for producing the same, and to a cosmetic composition containing the same as a active ingredient.

2. Related Arts

An organism needs protective barrier which prevents noxious foreign materials including microorganisms from external penetration, and counteracts the loss of body fluids such as water and blood, to maintain its life action. In case of human being, stratum corneum, the outermost layer of the epidermis, serves as this protective barrier. The stratum corneum prevents water within the skin from excessive evaporation, and controls penetration of foreign materials.

Dead, flat-shaped cells, corneocytes filled with keratin are embedded in the lipids of the intercellular domains to form membraneous bilayers. The corneocytes and the intercellular lipids make up the so-called permeable barrier. The intercellular space of the stratum corneum is mainly composed of glycolipids, cholesterol, free fatty acids and ceramides. Among them, the ceramides play an important role in maintaining well-balanced water content which is involved in skin elasticity, appearance and barrier functions.

The ceramides detected in human stratum corneum, which are represented by the following Formulae 3 to 9, contain sphingosine represented by the Formula 1 or phytosphingosine represented by the Formula 2 in the structure.

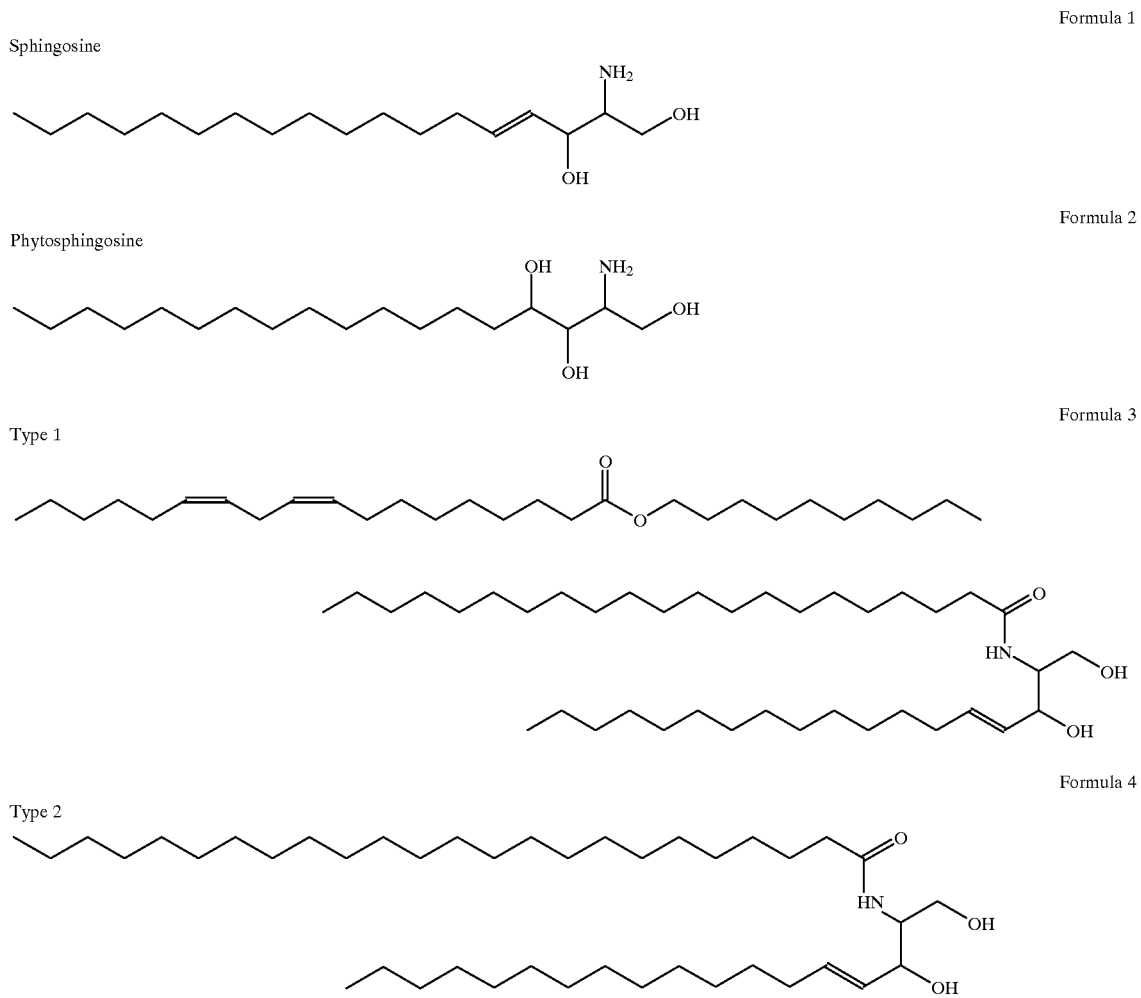

-continued

Type 3

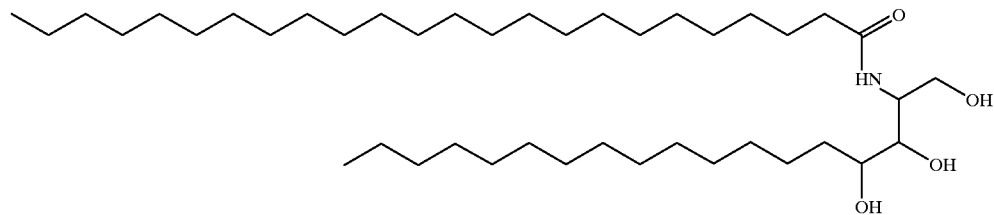

Formula 5

Type 4

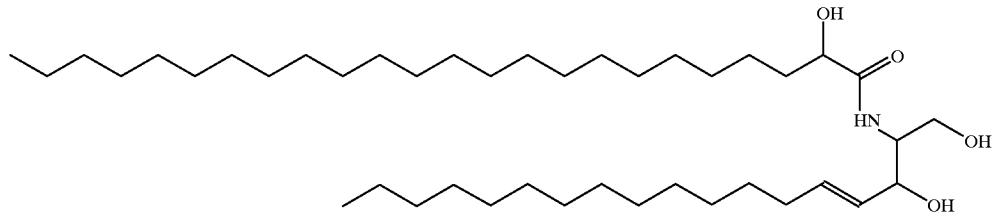

Formula 6

Type 5

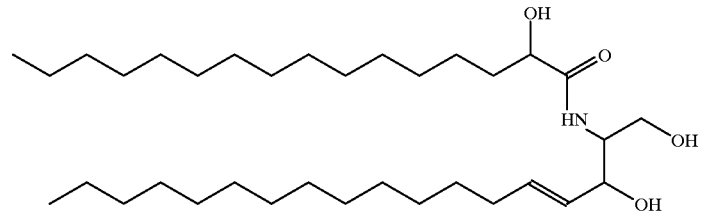

Formula 7

Type 6I

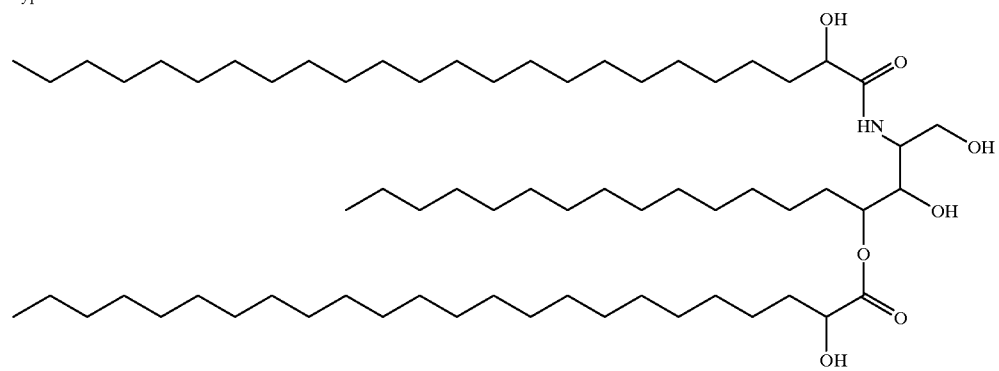

Formula 8

Type 6II

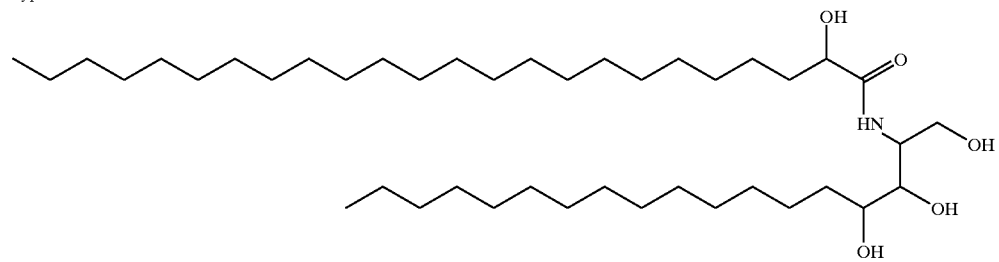

Formula 9

However, skin aging or skin damage caused by detergents which remove the lipids essential for the barrier function may disturb lipid synthesis and reduce ceramide content in the stratum corneum. Thus, cell cohesion may be weak and the stratum corneum cannot serve as a protective barrier. The skin may lose elasticity. As the ceramide content decreases, transepidermal water loss, direct exposure to the exterior irritation such as UV or chemicals, and peeling off of the stratum corneum may occur and thus the skin may be rough and damaged.

It has been reported that external application, such as cosmetics or pharmaceutical application, of ceramides can recover the lamella structure disturbed by skin aging or damage of the stratum corneum. Thus, stratum corneum can fully function as a protective barrier.

For the purpose of external application of ceramides, efforts have been made to find natural ceramides in animals, plants and microorganisms. As a result, various animals, plants and microorganisms containing natural ceramides were discovered. However, ceramide content of natural origin is very low. And it is difficult to isolate highly pure ceramides. Thus, supplies of natural ceramides by extraction thereof increase manufacturing cost and the price of final product. In addition, natural ceramides have low solubility in various organic solvents widely used in the cosmetics. That is to say, only small quantity of ceramides can be used in the cosmetics, which hinders providing their sufficient primary effects.

The present inventors have conducted extensive studies for the molecular structure of natural ceramides, in order to synthesize ceramide-like compounds which are structurally similar to natural ones. Natural ceramides have two long chain alkyl groups, amides, and hydroxyl groups. Considering this structural feature, molecular design was performed to synthesize ceramide-like compounds having two long chain alkyl groups, one or more amides and hydroxyl groups, and confirmed effectiveness in skin tonicity and recuperation after the composition containing the compound of the present invention had been applied onto the skin.

Skin ceramides form a stable lamella layer in the stratum corneum for their function as the skin barrier. Thus ceramide-like compounds should be also easily delivered into the intercellular space of the stratum corneum. Under this consideration, the present inventors introduced phosphoric or sulfuric group into the ceramide-like structures. The phosphoric or sulfuric group enhance the penetration through the skin surface. They are removed easily by enzymes, and then transformed into more stable lipophilic form.

SUMMARY OF THE INVENTION

Thus, an object of the present invention is to provide new ceramide-like compounds (I) represented by the following Formula 10:

Formula 10

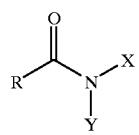

(I)

wherein,

R represents a $C_{9\sim31}$ linear or branched, saturated or unsaturated, hydroxylated or non-hydroxylated alkyl group, or a residue of 2-dodecen-1-yl succinic acid, X represents a group having a following structure:

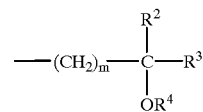

wherein, m is an integer from 1 to 3, inclusive;

$R^2$ and $R^3$, which may be the same or different, each represents H or a $C_{1\sim4}$ alkyl or hydroxyalkyl group; and $R^4$ represents $A^1$ or $-CH_2CH_2OA^1$, wherein $A^1$ represents H or any one of the following structures:

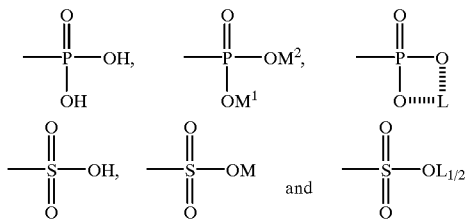

wherein,

M, $M^1$ and $M^2$ represent independently alkali metals or organic base containing nitrogen, and L represents an alkaline earth metal, Y represents a $C_{10\sim32}$ linear or branched, saturated or unsaturated, hydroxylated or non-hydroxylated alkyl group, or a group having following structure:

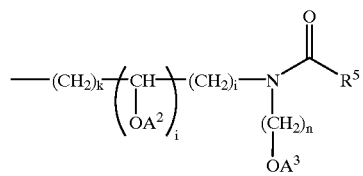

wherein, n is an integer from 1 to 3, inclusive;

k and i are independently an integer from 1 to 3, inclusive;

j is 0 or 1;

$R^5$ represents a $C_{9\sim31}$ linear or branched, saturated or unsaturated, hydroxylated or non-hydroxylated alkyl group;

$A^2$ and $A^3$ have the same meanings as $A^1$, independently.

Further, other object of the present invention is to provide a method for preparing the ceramide-like compounds (I).

Also, still other object of the present invention is to provide cosmetic compositions containing the ceramide-like compounds (I) as an active ingredient, which can increase moisture retention, skin tonicity and recuperation, and thereby can defer skin aging effectively.

The above and other objects and features of the present invention will be apparent to the skilled in the art from the following detailed description.

DETAILED DESCRIPTION OF THE INVENTION

The method of preparation of the compounds (I) according to the present invention will be described in more detail.

The compound (I-1a) represented by the following Formula 11, wherein R of Formula 10 are a $C_{9\sim31}$ saturated or unsaturated alkyl group, Y is a $C_{10\sim32}$ saturated or unsaturated alkyl group and X is —$CH_2CH_2OCH_2CH_2OH$:

Formula 11

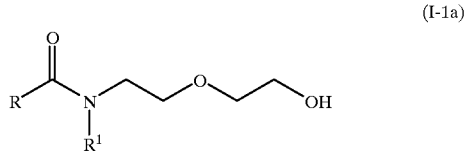

(I-1a)

wherein, R represents a $C_{9\sim31}$ linear or branched, saturated or unsaturated, hydroxylated or non-hydroxylated alkyl group and $R^1$ represents a $C_{10\sim32}$ linear or branched, saturated or unsaturated, hydroxylated or non-hydroxylated alkyl group; may be prepared by a process which comprises steps of:

(1) reacting an aliphatic amine with 2-(2-chloroethoxy) ethanol in ethanol, to produce a secondary amine derivative represented by the Formula (II):

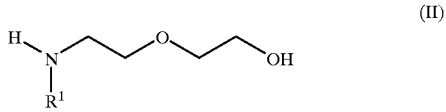

(II)

wherein, $R^1$ has the same meaning as defined in Formula (I-1a);

(2) reacting the secondary amine derivative of the step (1) with a $C_{10\sim32}$ fatty ester in the presence of an alkali catalyst, to produce an amide compound; and (3) dissolving the amide compound of the step (2) in an organic solvent such as chloroform or dichloroethane, and filtering off precipitates thus formed, and then recrystallizing a product from an organic solvent such as hexane or acetone.

In detail, the aliphatic amine employed in the step (1) is a primary amine having $C_{10\sim32}$ linear or branched, saturated or unsaturated, hydroxylated or non-hydroxylated alkyl group, and may include decylamine, undecylamine, dodecylamine, tridecylamine, tetradecylamine, hexadecylamine, octadecylamine, oleylamine and docosylamine.

The reaction of the step (1) may be performed at any temperature between 20° C. and 100° C. However, if the temperature is lower than 50° C., the reaction is very slow, while at a higher temperature than 90° C., tertiary amine is mainly obtained. Therefore, it is preferable to carry out the reaction at a temperature of 50~90° C. Thus produced secondary amine derivative of the Formula (II) is purified by recrystallizing from ethanol.

The compound (I-1a) can be prepared by reacting the intermediate (II) obtained in the step (1) with $C_{10\sim32}$ fatty ester under vigorous stirring for 2~5 hours, in the presence of an alkali catalyst.

The fatty ester employed in the step (2) is a methyl, ethyl or propyl ester of fatty acid having $C_{10\sim32}$ linear or branched, saturated or unsaturated, hydroxylated or non-hydroxylated alkyl group, and may include methyl decanoate, methyl undecanoate, methyl tridecanoate, methyl myristate, methyl pentadecanoate, methyl palmitate, methyl heptadecanoate, methyl stearate, methyl nonadecanoate, methyl eicosanoate, methyl docosanoate, ethyl decanoate, ethyl myristate, ethyl palmitate and ethyl stearate.

The reaction of the step (2) may be performed at any temperature between 80° C. and 200° C. However, if the temperature is lower than 110° C., the reaction is slow, while at temperature higher than 150° C., excessive by-products are produced. Therefore, it is preferable to carry out the reaction at a temperature of 110~150° C.

The solvent employed for the reaction may include dimethylformamide, dimethylacetamide, dimethylsulfoxide and other organic solvent having high boiling point. However, it is preferable that the reaction be carried out by melting the reacting materials by heating without using any solvent.

The alkali catalyst employed in the step (2) may include sodium carbonate, sodium bicarbonate, potassium carbonate, patassium bicarbonate sodium hydroxide and potassium hydroxide.

The ceramide-like compound (I-1a) exhibits good affinity to the stratum corneum, due to two long alkyl chains, and an amide and hydroxyl groups attached to the main chains. The compound makes dense lamella structure together with the lipids such as cholesterol and fatty acids within the intercellular space of the stratum corneum, and thus increases the moisture retention. Therefore, this compound (I-1a) is useful as a cosmetic active ingredient and the present invention can provide cosmetic compositions containing the compound (I-1a), which can increase moisture retention, skin tonicity and recuperation, thereby effectively defering skin aging.

Further, the compound (I-1b) represented by the following Formula 12:

Formula 12

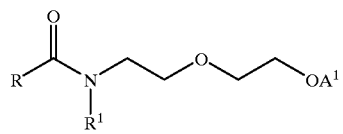

(I-1b)

wherein, R and $R^1$ have the same meanings as defined in Formula 11, independently, and $A^1$ has the same meaning as defined in Formula 10, except that $A^1$ is H; may be prepared by phosphorylating or sulfating the product (I-1a) of the step (3) and then neutralizing with alkali or base.

The phosphorylating reagent employed in the reaction may include phosphorus oxychloride and phosphoric anhydride. The sulfating reagent may include chlorosulfonic acid and sulfur trioxide.

Further, the neutralizing agent employed in the reaction may include alkali or metal oxides such as sodium hydroxide, potassium hydroxide, calcium hydroxide, magnesium hydroxide, calcium oxide and magnesium oxide; basic amino acids such as lysine, arginine and histidine; ammonia or amines such as triethanol amine; cationic polymers such as polyquaternium-4, -6, -7, -10, -11 and -16; and cationic surfactants such as lauryldimethylbenzyl ammonium chloride and stearyldimethylbenzyl ammonium chloride.

The compound (I-1b) has phosphoric or sulfuric group having good affinity to cellular membranes and easily released from the ceramide structure by enzymes within the stratum corneum. That is, the ceramide-like compounds having phosphoric or sulfuric group such as compound (I-1b) exhibit ionic properties. Such ionic properties render them higher solubility, and make delivery into the stratum corneum much easier. And, the compounds once absorbed into the stratum corneum may be decomposed by enzymes to release phosphoric or sulfuric group. The decomposed compounds have lower solubility than original compounds, and thereby can be stabilized within the lamella structure together with other intracellular lipids. Therefore, the ceramide-like compounds having phosphoric or sulfuric group such as compound (I-1b) are useful as a cosmetic active ingredient, and the present invention can provide cosmetic compositions containing these compounds, which can increase moisture retention, skin tonicity and recuperation, thereby effectively defering the skin-aging process.

The compound (I-2a) represented by the following Formula 13, wherein R of Formula 10 is a residue of 2-dodecen-1-yl succinic acid, Y is a $C_{10-32}$ saturated or unsaturated alkyl group, and X is —$CH_2CH_2OCH_2CH_2OH$:

Formula 13

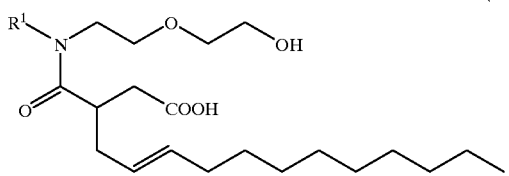
(I-2a)

wherein, $R^1$ represents a $C_{10-32}$ linear or branched, saturated or unsaturated, hydroxylated or non-hydroxylated alkyl group; may be prepared by a process which comprises steps of:
 (1) reacting an aliphatic amine with 2-(2-chloroethoxy) ethanol in ethanol, to produce a secondary amine derivative represented by the Formula (II):

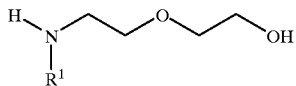
(II)

wherein, $R^1$ has the same meaning as defined in Formula (I-2a);
 (2) reacting the secondary amine derivative of the step (1) with 2-dodecen-1-yl succinic anhydride, to produce an amide compound; and
 (3) removing the solvent by evaporation, and then subjecting a residue to a column chromatography.

In detail, the aliphatic amine employed in the step (1) is a primary amine having $C_{10-32}$ linear or branched, saturated or unsaturated, hydroxylated or non-hydroxylated alkyl group, and may include decylamine, undecylamine, dodecylamine, tridecylamine, tetradecylamine, hexadecylamine, octadecylamine, oleylamine and docosylamine.

The reaction of the step (1) may be performed at any temperature between 20° C. and 100° C. However, if the temperature is lower than 50° C., the reaction is slow, while at a temperature higher than 90° C., tertiary amine is mainly obtained. Therefore, it is preferable to carry out the reaction at a temperature of 50~90° C. Thus produced secondary amine derivative of the formula (II) is purified by recrystallizing from ethanol.

The compound (I-2a) can be prepared by reacting the intermediate (II) obtained from step (1) with 2-dodecen-1-yl-succinic anhydride under vigorous stirring for 3~6 hours.

The reaction of the step (2) may be performed at any temperature between 10° C. and 80° C. However, if the temperature is lower than 20° C., the reaction is very slow, while at a temperature higher than 50° C., excessive by-products is obtained. Therefore, it is preferable to carry out the reaction at a temperature of 20~50° C.

Further, the compound (I-2b) represented by the following Formula 14, may be prepared by phosphorylating or sulfating the product (I-2a) of the step (3), and then neutralizing with alkali or base:

Formula 14

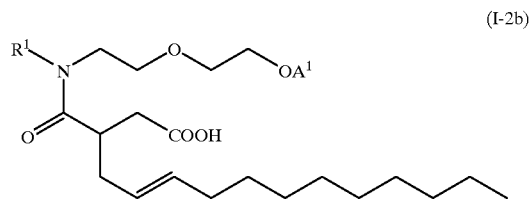
(I-2b)

wherein, $R^1$ has the same meaning as defined in Formula 13 and $A^1$ has the same meaning as defined in Formula 10, except that $A^1$ is H.

The compound (I-3a) represented by the following Formula 15, wherein R of Formula 10 is a $C_{9-31}$ saturated or unsaturated alkyl group; X is a hydroxyalkyl group wherein $R^2$, $R^3$ and $R^4$ are all H; and Y is a group having the same structural features as defined in Formula 10 wherein j is 0, n is the same integer as m of X, and $A^3$ is H:

Formula 15

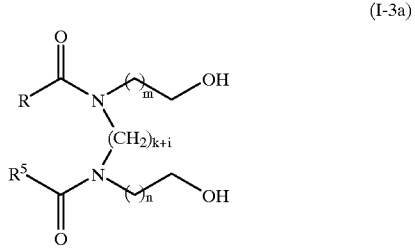
(I-3a)

wherein, both R and $R^5$, which may be the same or different, each represents a $C_{9-31}$ linear or branched, saturated or unsaturated, hydroxylated or non-hydroxylated alkyl group, m is an integer from 1 to 3, inclusive, k+i is an integer from 2 to 6, inclusive, and n is the same integer as m; may be prepared by a process which comprises steps of:
 (1) reacting a primary amino alcohol such as ethanolamine, 3-amino-1-propanol and 4-aminobutanol, with a $C_{2-6}$ alkyl dihalide in ethanol, to produce a secondary amino alcohol derivative represented by the Formula (III):

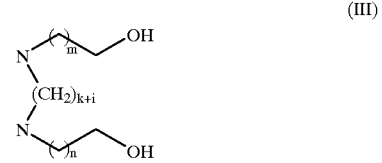
(III)

wherein, m, n and k+i have the same meanings as defined in said Formula (I-3a), respectively;
 (2) reacting the secondary amino alcohol derivative of the step (1) with a $C_{10-32}$ fatty acid chloride in the presence of an alkali catalyst, to produce a diamide compound; and (3) dissolving the diamide compound of the step (2) in an organic solvent such as chloroform or dichloromethane, and filtering off precipitates thus formed, and then recrystallizing a product from an organic solvent such as acetone, chloroform/acetone or chloroform/hexane.

In detail, in the step (1), the primary amino alcohol having a $C_{1\sim5}$ saturated chain may be employed. It is also preferable to react 6~10 moles of the primary amino alcohol per mole of alkyl dihalide. If the amount of the amino alcohol is lower than 6 mole, the yield is decreased and by-product such as tertiary amine is obtained.

The reaction of the step (1) may be performed at any temperature between 0° C. and 80° C. However, if the temperature is lower than 40° C., the reaction is very slow, while at a temperature higher than 80° C., tertiary amine is mainly obtained. Therefore, it is preferable to carry out the reaction at a temperature of 40~80° C. Thus, secondary amino alcohol derivative of the Formula (III) is obtained by recrystallizating from ethanol/chloroform/hexane, after removing the solvent and the unreacted primary amino alcohol by vacuum evaporation.

The compound (I-3a) can be prepared by reacting the intermediate (III) obtained in the step (1) with a $C_{10\sim32}$ fatty acid chloride in the mixed solvent of distilled water and dioxane, under vigorous stirring, for about 2~5 hours, in the presence of an alkali catalyst.

The reaction of the step (2) may be performed at any temperature between 0° C. and 40° C. Preferably, the reaction is carried out at a temperature of 10~30° C.

As a solvent for the reaction, distilled water or other polar solvent may be employed. Examples of the polar solvent may include tetrahydrofuran, dioxane, dimethylformamide, dimethylacetamide, dimethylsulfoxide. Among them, dioxane and tetrahydrofuran are preferably employed.

Further, the alkali catalyst employed in the step (2) may include magnesium oxide, calcium oxide, potassium carbonate, sodium hydroxide and potassium hydroxide.

Further, the compound (I-3b) represented by the following Formula 16, having similar structure to that of the compound (I-3a):

Formula 16

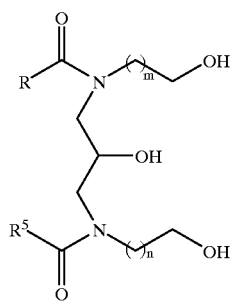
(I-3b)

wherein, R, $R^5$, m and n have the same meanings as defined in Formula 15, respectively; may be prepared by the same process as described in the preparation of the compound (I-3a), except that alkyl dihalide is replaced by 1,3-dichloro-2-hydroxypropane or epichlorohydrin.

Further, ceramide-like compounds wherein one or more hydroxyl groups of the compound (I-3a) or (I-3b) are phosphorylated or sulfated may be obtained by phosphorylating or sulfating the compound (I-3a) or (I-3b), and then neutralizing with alkali or base.

In summary, the compound (I-3) represented by the following Formula 17:

Formula 17

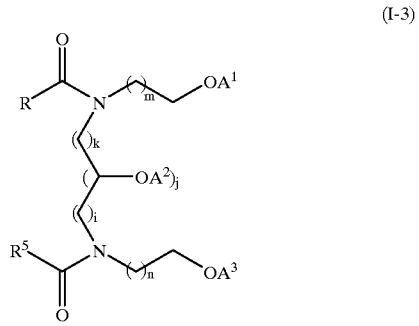
(I-3)

wherein, R and $R^5$ have the same meanings as defined in Formula 15, independently, and $A^1$, $A^2$, $A^3$, i, j, k, m and n have the same meanings as defined in Formula 10, respectively; may be prepared by a process which comprises steps of:

(1) reacting a primary amino alcohol such as ethanolamine, 3-amino-1-propanol and 4-aminobutanol, with a dihalo compound or a monohalo epoxy compound in ethanol, to produce a secondary amino alcohol derivative represented by the Formula (IV):

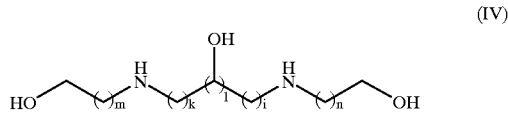
(IV)

wherein, i, j, k, m and n have the same meanings as defined in said Formula (I-3), respectively;

(2) reacting the secondary amino alcohol derivative of the step (1) with a $C_{10\sim32}$ fatty acid chloride in the presence of an alkali or organic base as a catalyst, to produce a diamide compound;

(3) dissolving the diamide compound of the step (2) in an organic solvent, and filtering off precipitates, and then recrystallizing a product from an organic solvent such as acetone, chloroform/acetone or chloroform/hexane;

(4) phosphorylating or sulfating the diamide compound obtained in the step (3); and then (5) neutralizing the product of the step (4) with alkali or base.

In detail, the dihalo compound employed in the step (1) may include 1,3-dichloro-2-propanol, 1,3-dibromo-1-propanol, 1,2-dichloroethane and 1,2-dibromoethane. And, the monohalo epoxy compounds may include epichlorohydrin, epibromohydrin, 3,4-epoxy-1-chlorobutane, 3,4-epoxy-1-bromo butane, 4,5-epoxy-1-chloropentane and 4,5-epoxy-1-bromopentane.

Further, the alkali catalyst employed in the step (2) may include potassium hydroxide, sodium hydroxide, magnesium hydroxide, calcium hydroxide, sodium carbonate, potassium carbonate, magnesium oxide and calcium oxide. And, the organic base may include trimethylamine and pyridine.

The organic solvent employed in the step (3) may include alcohols such as methanol, ethanol, propanol and isopropanol; halo compounds such as dichloromethane, chloroform, 1,2-dichloroethane and carbon tetrachloride; hydrocarbons such as n-hexane, cyclohexane, benzene and toluene.

The phosphorylating reagent employed in the step (4) may include phosphorus oxychloride and phosphoric anhydride. The sulfating reagent may include chlorosulfonic acid and sulfur trioxide.

Further, the neutralizing agent employed in the step (5) may include alkali or metal oxides such as sodium hydroxide, potassium hydroxide, calcium hydroxide, magnesium hydroxide, calcium oxide and magnesium oxide; basic amino acids such as lysine, arginine and histidine; ammonia or amines such as triethanol amine; cationic polymers such as polyquaternium-4, -6, -7, -10, -11 and -16; and cationic surfactants such as lauryldimethylbenzyl ammonium chloride and stearyldimethylbenzyl ammonium chloride.

The ceramide-like compounds of the present invention, such as compounds (I-1) to (I-3), exhibit good affinity to the stratum corneum, due to two long chain alkyl groups and amide and hydroxyl groups attached to the main chains. These compounds make the lamella structure denser together with various lipids including cholesterol and fatty acids within the intercellular space of the stratum corneum, and thus increase the moisture retention. In particular, the ceramide-like compounds having phosphoric or sulfuric group such as compounds (I-1b), (I-2b) and (I-3) exhibit ionic properties. Due to these ionic properties, these compounds have higher solubility than natural ceramides, which makes delivery into the stratum corneum easier. And, the compounds once absorbed into the stratum corneum may be decomposed by enzyme to release phosphoric or sulfuric group. The decomposed compounds have lower solubility than original compounds, and thereby can be stabilized within the lamella structure together with various lipids.

Therefore, these ceramide-like compounds of the present invention are useful as a cosmetic active ingredient. The ceramide-like compounds of the present invention may be incorporated in the epidermal composition such as cosmetic composition, which can increase moisture retention, skin tonicity and recuperation, and thereby can defer skin aging effectively. The composition may contain the ceramide-like compounds in an amount of 0.001~20% by weight, preferably 0.1~10% by weight, which can be chosen depending on the formulations or the final purposes of the composition. Further, the ceramide-like compounds of the present invention may be formulated, but not limited thereto, skin softners, astringents, nutrient toilet water, nutrient creams, massage creams, essences, eye essences, eye creams, cleansing creams, cleansing foams, cleansing water, packs, powders and the like.

PREFERRED EMBODIMENT OF THE INVENTION

The present invention will be described in more detail by way of the following examples. However, these examples are provided for only illustration purpose and should not be construed as limiting the scope of the invention, which is properly delineated in the accompanying claims.

EXAMPLE 1

Preparation of N-(2-hydroxyethoxy)ethyl-n-hexadecylamine

Into a 1 l rounded-flask, were introduced 48.2 g of hexadecyl amine and 700 ml of ethanol. The mixture was heated to reflux, and then was gradually added 11 ml of 2-(2-chloroethoxy)ethanol. The mixture was refluxed for 3 hours and cooled to a room temperature. Thereto was added solution of KOH/ethanol to produce precipitates, which were removed by filtration. The filtrate was concentrated under reduced pressure, and then was recrystallized from ethanol, and dried to give 24.1 g of the title compound (Yield: 70%) as white powder, which was identified by IR and NMR. The results are shown in Table 1.

EXAMPLE 2

Preparation of N-(2-hydroxyethyloxy)ethyl-n-oleylamine

The procedure described in Example 1 was followed by employing 53.5 g of oleyl amine, instead of hexadecyl amine of Example 1, to give 22.0 g of the title compound (Yield: 59%), which was identified by IR and NMR. The results are shown in Table 1.

EXAMPLE 3

Preparation of N-(2-hydroxyethoxy)ethyl-n-octadecylamine

The procedure described in Example 1 was followed by employing 53.9 g of octadecyl amine, instead of hexadecyl amine of Example 1, to give 26.2 g of the title compound (Yield: 70%) as white powder, which was identified by IR and NMR. The results are shown in Table 1.

EXAMPLE 4

Preparation of N-hexadecyl-N-(2-hydroxyethoxy)ethyl hexadecanamide

Into a 250 ml-flask equipped with reflux condenser, were introduced 14.3 g of methyl palmitate and 16.5 g of N-(2-hydroxyethoxy)ethyl-n-hexadecyl amine prepared in Example 1, and thereto was added 2.6 g of sodium carbonate. Then, the mixture was stirred violently for 3 hours at 120° C. After the termination of the reaction, the mixture was cooled to a room temperature and 100 ml of chloroform was added thereto to be dissolved. The precipitates were removed and the solvent was evaporated off under reduced pressure. The produced solid was recrystallized from hexane to give 23.2 g of the title compound(Yield: 82%) as white powder, which was identified by IR and NMR. The results are shown in Table 1.

EXAMPLE 5

Preparation of N-oleyl-N-(2-hydroxyethoxy)ethyl hexadecanamide

The procedure described in Example 4 was followed by employing 17 g of N-(2-hydroxyethoxy)ethyl-n-oleylamine prepared in Example 2, instead of N-(2-hydroxyethoxy)ethyl-n-hexadecyl amine of Example 4, to give 22.6 g of the title compound(Yield: 73%) as white powder, which was identified by IR and NMR. The results are shown in Table 1.

EXAMPLE 6

Preparation of N-octadecyl-N-(2-hydroxyethoxy)ethyl hexadecanamide

The procedure described in Example 4 was followed by employing 17.2 g of N-(2-hydroxyethoxy)ethyl-n-octadecylamine prepared in Example 3, instead of N-(2-hydroxyethoxy)ethyl-n-hexadecyl amine of Example 4, to give 24.2 g of the title compound(Yield: 78%) as white powder, which was identified by IR and NMR. The results are shown in Table 1.

EXAMPLE 7
Preparation of N-hexadecyl-N-(2-hydroxyethoxy)ethyl tetradecanamide The procedure described in Example 4 was followed by employing 13.3 g of methyl myristate, instead of methyl palmitate of Example 4, to give 20.5 g of the title compound (Yield: 76%) as white powder, which was identified by IR and NMR. The results are shown in Table 1.

EXAMPLE 8
Preparation of (N-hexadecyl-N-(2-hydroxyethoxy)ethyl)-3-(2-dodecen-1-yl)carboxyamidopropionic acid Into a 250 ml-flask, were introduced 14.6 g of 2-dodecen-1-yl-succinic anhydride and 16.5 g of N-(2-hydroxyethoxy)ethyl-n-hexadecylamine prepared in Example 1. 120 ml of chloroform was added thereto and the mixture was heated to 40° C. to be dissolved. The obtained mixture was stirred for 4 hours at the same temperature and the solvent was evaporated off under reduced pressure. The residue was subjected to silica gel column chromatography to give 18.1 g of the title compound(Yield: 61%) as pale yellow powder, which was identified by IR and NMR. The results are shown in Table 1.

EXAMPLE 9
Preparation of (N-oleyl-N-(2-hydroxyethoxy)ethyl)-3-(2-dodecen-1-yl)carboxamidopropionic acid The procedure described in Example 8 was followed by employing 17 g of N-(2-hydroxyethoxy)ethyl-n-oleylamine prepared in Example 2, instead of N-(2-hydroxyethoxy)ethyl-n-hexadecylamine of Example 8, to give 18.6 g of the title compound(Yield: 60%) as pale yellow powder, which was identified by IR and NMR. The results are shown in Table 1.

EXAMPLE 10
Preparation of (N-octadecyl-N-(2-hydroxyethoxy)ethyl)-3-(2-dodecen-1-yl)carboxamidopropionic acid The procedure described in Example 8 was followed by employing 17.2 g of N-(2-hydroxyethoxy)ethyl-n-octadecylamine prepared in Example 3, instead of N-(2-hydroxyethoxy)ethyl-n-hexadecylamine of Example 8, to give 20.3 g of the title compound(Yield: 65%) as pale yellow powder, which was identified by IR and NMR. The results are shown in Table 1.

EXAMPLE 11
Preparation of (N-tetradecyl-N-(2-hydroxyethoxy)ethyl-3-(2-dodecen-1-yl)carboxamidopropionic acid The procedure described in Example 1 was followed by employing 42.6 g of tetradecyl amine, instead of hexadecyl amine of Example 1, to give 22.4 g of N-(2-hydroxyethoxy)ethyl-n-tetradecylamine.

Subsequently, the procedure described in Example 8 was followed by employing 17 g of N-(2-hydroxyethoxy)ethyl-n-tetradecylamine prepared above, instead of N-(2-hydroxyethoxy)ethyl-n-hexadecylamine of Example 8, to give 17.2 g of the title compound(Yield: 59%) as pale yellow powder, which was identified by IR and NMR. The results are shown in Table 1.

TABLE 1

| Compounds | | $^{1}$H-NMR ($\delta$, ppm) | IR (cm$^{-1}$) | $^{13}$C-NMR (ppm) |
|---|---|---|---|---|
| Ex. | 1 | 0.9(3H, t), 1.2(28H, s), 2.6(2H, m), 2.8(2H, t), 3.5(6H, m). | 3342, 2918 1472 | |
| | 2 | 0.9(3H, t), 1.2(24H, s), 2.0(4H, m), 2.6(2H, m), 2.8(2H, t), 3.5(6H, m), 5.3(2H, m) | 3340, 2915 1650, 1465 | |
| | 3 | 0.9(3H, t), 1.2(32H, s), 2.6(2H, m), 2.8(2H, t), 3.5(6H, m) | 3342, 2916 1472 | |
| | 4 | 0.9(6H, t), 1.2(54H, s), 2.3(2H, m), 3.2(2H, m), 3.3~3.6(8H, m) | 3290, 2915 1470, 1618 | 181 |
| | 5 | 0.9(6H, t), 1.2(50H, s), 2.1(4H, m), 2.3(2H, m), 3.2(2H, m), 3.3~3.6(8H, m) 5.3(2H, m) | 3295, 2914 1472, 1620 | 180 129~131 (C=C) |
| | 6 | 0.9(6H, t), 1.2(58H, s), 2.3(2H, m), 3.2(2H, m), 3.3~3.7(8H, m) | 3300, 2918 1468, 1615 | 181 |
| | 7 | 0.9(6H, t), 1.2(50H, s). 2.4(2H, m), 3.2(2H, m), 3.4~3.6(6H, m) | 3300, 2917 1469, 1620 | 181 |
| | 8 | 0.9(6H, t), 1.2(42H, s), 2.1~2.4(6H, br), 2.7(1H, m), 3.0~3.2(4H, br), 3.5(6H, m) 5.3(2H, m) | 3294, 2917 1470, 1618 | 181 |
| | 9 | 0.9(6H, t), 1.2(38H, s), 2.2~2.4(10H, br), 2.6(1H, m), 3.1(2H, m), 3.2~3.6(8H, br) 5.3(4H, m) | 3295, 2915 1471, 1620 | 180 129~131 (C=C) |
| | 10 | 0.9(6H, t), 1.2(46H, s), 2.2~2.4(6H, m), 2.6(1H, m), 3.1~3.3(4H, br), 3.5(6H, m) 5.3(2H, m) | 3299, 2918 1465, 1616 | 181 |
| | 11 | 0.9(6H, t), 1.2(38H, s), 2.1~2.4(6H, br), 2.6(1H, m), 3.0~3.3(4H, br), 3.6(6H, m), 5.4(2H, m) | 3303, 2917 1466, 1621 | 181 |

EXAMPLE 12
Preparation of N-(2-hydroxypropane)-N-hexadecyl amine

Into a 1 l rounded-flask, were introduced 48.2 g of hexadecyl amine and 700 ml of ethanol. Thereto were gradually added 18.9 g of 1-chloro-2-propanol at 40° C. The obtained mixture was stirred for 3 hours at the same temperature. Thereto was added solution of KOH/ethanol to produce precipitates, which were removed by filtration. The filtrate was concentrated under reduced pressure and then recrystallized from ethanol to give 36 g of the title compound(Yield: 60%) as white powder, which was identified by IR and NMR. The results are shown in Table 2.

EXAMPLE 13
Preparation of N-(2-methyl-2-hydroxypropane)-N-hexadecyl amine

The procedure described in Example 12 was followed by employing 22.6 g of 1-chloro-2-methyl-2-propanol, instead of 1-chloro-2-propanol of Example 12, to give 48.3 g of the title compound(Yield: 77%) as white powder, which was identified by IR and NMR. The results are shown in Table 2.

EXAMPLE 14
Preparation of N-(2-ethoxy-2-hydroxyethane)-N-hexadecyl amine

The procedure described in Example 12 was followed by employing 23.2 g of 1-chloro-2-ethoxy-2-ethanol, instead of 1-chloro-2-propanol of Example 12, to give 45.6 g of the title compound(Yield: 69%) as white powder, which was identified by IR and NMR. The results are shown in Table 2.

EXAMPLE 15
Preparation of N-(2-hydroxypropane)-N-oleyl amine

The procedure described in Example 12 was followed by employing 53.5 g of oleyl amine, instead of hexadecyl amine of Example 12, to give 35.2 g of the title compound (Yield: 78%) as white powder, which was identified by IR and NMR. The results are shown in Table 2.

EXAMPLE 16
Preparation of N-(2-methyl-2-hydroxypropane)-N-oleyl amine

The procedure described in Example 13 was followed by employing 53.5 g of oleyl amine, instead of hexadecyl amine of Example 13, to give 35.2 g of the title compound (Yield: 78%) as white powder, which was identified by IR and NMR. The results are shown in Table 2.

EXAMPLE 17
Preparation of N-hexadecyl-N-(2-hydroxypropane) hexadecanamide

Into a 250 ml-flask equipped with reflux condenser, were introduced 14.3 g of methyl palmitate and 16 g of N-(2-hydroxypropane)-N-hexadecyl amine prepared in Example 12, and thereto was added 2.6 g of sodium carbonate. Then, the mixture was stirred violently for 3 hours at 120° C. After the termination of the reaction, the mixture was cooled to a room temperature and 100 ml of chloroform was added. The precipitates thus formed were removed and the solvent was evaporated off under reduced pressure. The residue was recrystallized from hexane to give 21.6 g of the title compound(Yield: 80%) as white powder, which was identified by IR and NMR. The results are shown in Table 2.

EXAMPLE 18
Preparation of N-hexadecyl-N-(2-methyl-2-hydroxypropane)hexadecanamide The procedure described in Example 17 was followed by employing 14.9 g of methyl palmitate and 15.7 g of N-(2-methyl-2-hydroxypropane)-N-hexadecyl amine prepared in Example 13, to give 24.6 g of the title compound(Yield: 87%) as white powder, which was identified by IR and NMR. The results are shown in Table 2.

EXAMPLE 19
Preparation of N-hexadecyl-N-(2-ethoxy-2-hydroxyethane) hexadecanamide The procedure described in Example 17 was followed by employing 14.9 g of methyl palmitate and 16.5 g of N-(2-ethoxy-2-hydroxyethane)-N-hexadecyl amine prepared in Example 14, to give 24.2 g of the title compound (Yield: 83%) as white powder, which was identified by IR and NMR. The results are shown in Table 2.

EXAMPLE 20
Preparation of N-oleyl-N-(2-hydroxypropane) hexadecanamide

The procedure described in Example 17 was followed by employing 14.9 g of methyl palmitate and 16.3 g of N-(2-hydroxypropane)-N-oleyl amine prepared in Example 15, to give 21.6 g of the title compound(Yield: 78%) as white powder, which was identified by IR and NMR. The results are shown in Table 2.

EXAMPLE 21
Preparation of N-oleyl-N-(2-methyl-2-hydroxypropane) hexadecanamide The procedure described in Example 17 was followed by employing 14.9 g of methyl palmitate and 17 g of N-(2-methyl-2-hydroxypropane)-N-oleyl amine prepared in Example 16, to give 21 g of the title compound(Yield: 71%) as white powder, which was identified by IR and NMR. The results are shown in Table 2.

EXAMPLE 22
Preparation of (N-hexadecyl-N-palmitoyl)-1-aminopropane-2-sodium phosphate 5.38 g of N-hexadecyl-N-(2-hydroxypropane) hexadecanamide prepared in Example 17 and 1.15 g of phosphoric acid were added to 100 ml of dioxane and then stirred for 1 hours. 2.0 g of phosphorus pentoxide was added thereto and then was refluxed for 5 hours. After the termination of the reaction, the mixture was cooled to a room temperature and then 3.8 ml of 40% NaOH was added thereto. The solvent was evaporated off under reduced pressure. Then, ethanol was added to the reaction mixture, and precipitates thus produced were removed by filtration. The filtrate was concentrated under reduced pressure and was subjected to silica gel column chromatographied to give 4.1 g of the title compound(Yield: 66%), which was identified by IR and NMR. The results are shown in Table 2.

EXAMPLE 23
Preparation of (N-hexadecyl-N-palmitoyl)-1-amino-2-methylpropane-2-sodium phosphate The procedure described in Example 22 was followed by employing 5.7 g of N-hexadecyl-N-(2-methyl-2-hydroxypropane)hexadecanamide prepared in Example 18, instead of N-hexadecyl-N-(2-hydroxypropane) hexadecanamide of Example 22, to give 4.3 g of the title compound(Yield: 64%), which was identified by IR and NMR. The results are shown in Table 2.

EXAMPLE 24
Preparation of (N-hexadecyl-N-palmitoyl)-1-amino-2-ethoxyethane-2-sodium phosphate The procedure described in Example 22 was followed by employing 5.8 g of N-hexadecyl-N-(2-ethoxy-2-hydroxyethane)hexadecanamide prepared in Example 19, instead of N-hexadecyl-N-(2-hydroxypropane) hexadecanamide of Example 22, to give 4.4 g of the title compound(Yield: 64%), which was identified by IR and NMR. The results are shown in Table 2.

EXAMPLE 25
Preparation of (N-oleyl-N-palmitoyl)-1-aminopropane-2-sodium sulfate 5.8 g of N-oleyl-N-(2-hydroxypropane)hexadecanamide prepared in Example 20 was added to 100 ml of dioxane, and then 1.3 g of chlorosulfonic acid was added slowly thereto at 10~15° C. After the addition, the mixture was stirred for 2 hours at a room temperature. After the termination of the reaction, 3 ml of 40% NaOH was added thereto. The solvent was evaporated off under reduced pressure. Then, ethanol was added to the reaction mixture, and precipitates thus produced were removed by filtration. The filtrate was concentrated under reduced pressure and subjected to silica gel column chromatography to give 4.9 g of the title compound (Yield: 72%), which was identified by IR and NMR. The results are shown in Table 2.

EXAMPLE 26
Preparation of (N-oleyl-N-palmitoyl)-1-amino-2-methylpropane-2-sodium sulfate The procedure described in Example 25 was followed by employing 5.9 g of N-oleyl-N-(2-methyl-2-hydroxypropane)hexadecanamide prepared in Example 21, instead of N-oleyl-N-(2-hydroxypropane)hexadecanamide of Example 25, to give 5.1 g of the title compound(Yield: 73%), which was identified by IR and NMR. The results are shown in Table 2.

mixture was refluxed for 4 hours, and then cooled to a room temperature. Thereto was added 56 g of solution of 10% KOH/ethanol to produce precipitates, which were removed by filtration. The solvent and unreacted ethanolamine were evaporated off under reduced pressure, and the residue was recrystallized from ethanol, chloroform and hexane. The product was filtered and dried under reduced pressure to give 13.1 g of N,N'-bis(2-hydroxyethyl)-N1,2-diaminoethane.

Into other 500 ml rounded-flask, were introduced 4.0 g of magnesium oxide and 80 g of distilled water. The mixture was stirred. Thereto was added 7.3 g of N,N'-bis(2-hydroxyethyl)-1,2-diaminoethane prepared above and 250 ml of 1,4-dioxane. 27.5 g of palmitoyl chloride was gradually added dropwise to the resulting mixture for 1 hour under violent stirring at a room temperature. After stirring for 2 hours, the mixture was filtered, and then the filtrate was mixed with 200 ml of chloroform and washed twice with 200 ml of distilled water. Organic phase was cooled to produce solid material, which was recovered by filtration. The solid material was dried and recrystallized from chloroform/acetone and chloroform/hexane, to give 24.3 g of the title compound as white powder, which was identified by IR and NMR. The results are shown in Table 3.

EXAMPLE 28
Preparation of 1,2-bis(N-(2-hydroxyethyl)-lauroylamino)ethane

TABLE 2

| Compounds | | $^1$H-NMR (δ, ppm) | IR (cm$^{-1}$) | $^{13}$C-NMR (ppm) |
|---|---|---|---|---|
| Ex. | 12 | 0.9(3H, t), 1.1(31H, s), 3.0(2H, m), 3.4(2H, d), 3.6(1H, m) | 3342, 2916, 1471 | |
| | 13 | 0.9(3H, t), 1.2(34H, s), 3.1(4H, m) | 3340, 2915, 1467 | |
| | 14 | 0.9(3H, t), 1.1(28H, s), 3.1(4H, m), 3.3~3.5(6H, br) | 3342, 2918, 1472 | |
| | 15 | 0.9(3H, t), 1.2(23H, s), 2.1(4H, m), 3.1(2H, m), 3.4(2H, d), 3.6(1H, m), 5.3(2H, t) | 3338, 2918, 1470 | 129~131 (C=C) |
| | 16 | 0.9(3H, t), 1.2(34H, s), 3.1(4H, m) | 3339, 2916, 1472 | 129~131 (C=C) |
| | 17 | 0.9(6H, t), 1.2(57H, s), 2.4(2H, m), 3.0(2H, m), 3.4(2H, d), 3.7(1H, m) | 3300, 2918, 1472 1615 | 180 |
| | 18 | 0.9(6H, t), 1.2(60H, s), 2.4(2H, m), 3.1(4H, m) | 3300, 2918, 1472 1620 | 180 |
| | 19 | 0.9(6H, t), 1.2(54H, s), 2.3(2H, m), 3.1(4H, m), 3.6(6H, d) | 3300, 2918, 1472 1620 | 181 |
| | 20 | 0.9(6H, t), 1.2(50H, s), 2.2(4H, m), 2.7(2H, m), 3.1(2H, m), 3.4(2H, d), 3.6(1H, m), 5.4(2H, m) | 3300, 2918, 1472 1620 | 181 129~131 (C=C) |
| | 21 | 0.9(6H, t), 1.2(54H, s), 2.3(2H, m), 3.1(4H, m), 3.6(6H, d) | 3300, 2918, 1472 1620 | 181 129~131 (C=C) |
| | 22 | 0.9(6H, t), 1.2(57H, s), 2.4(2H, m), 3.1(2H, m), 3.4(2H, d), 3.7(1H, m) | 3300, 2917, 1471 1615, 1371, 1175 | 180 |
| | 23 | 0.9(6H, t), 1.2(60H, s), 2.4(2H, m), 3.1(4H, m) | 3300, 2918, 1472 1621, 1373, 1174 | 180 |
| | 24 | 0.9(6H, t), 1.2(54H, s), 2.3(2H, m), 3.1(4H, m), 3.7(6H, d) | 3298, 2917, 1470 1620, 1373, 1175 | 181 |
| | 25 | 0.9(6H, t), 1.2(57H, s), 2.4(2H, m), 3.1(2H, m), 3.4(2H, d), 3.7(1H, m) | 3300, 2917, 1471 1617 | 180 |
| | 26 | 0.9(6H, t), 1.2(60H, s), 2.4(2H, m), 3.1(4H, m) | 3300, 2918, 1472 1619 | 181 |

EXAMPLE 27
Preparation of 1,2-bis(N-(2-hydroxyethyl)-palmitoylamino)ethane

Into a 500 ml rounded-flask equipped with reflux condenser, were introduced 48.9 g of ethanolamine and 200 ml of ethanol. The mixture was stirred well, and then 18.8 g of 1,2-dibromoethane was added dropwise for 1 hours. The Into a 500 ml rounded-flask, were introduced 4.0 g of magnesium oxide and 80 g of distilled water. The mixture was stirred. Thereto was added 7.3 g of N,N'-bis(2-hydroxyethyl)-1,2-diaminoethane prepared in Example 27, and then was added 250 ml of 1,4-dioxane. 21.3 g of lauroyl chloride was gradually added dropwise to the resulting mixture for 1 hour under violent stirring at a room temperature. After stirring for 2 hours, the mixture was filtered, and the filtrate was mixed with 200 ml of chloroform, and washed twice with 200 ml of distilled water. The organic phase was cooled to produce solid material, which was recovered by filtration. The solid material was dried and recrystallized from acetone, to give 19.5 g of the title compound as white powder, which was identified by IR and NMR. The results are shown in Table 3.

EXAMPLE 29

Preparation of 1,2-bis(N-(2-hydroxyethyl)-oleoylamino) ethane

The procedure described in Example 28 was followed by employing 29.3 g of oleoyl chloride, instead of lauoyl chloride of Example 28, to give 27.2 g of the title compound as white powder, which was identified by IR and NMR. The results are shown in Table 3.

EXAMPLE 30

Preparation of N,N'-bis(2-hydroxyethyl)-N-palmitoyl-N'-oleoyl-1,2-diaminoethane

Into a 500 ml rounded-flask, were introduced 4.0 g of magnesium oxide and 80 g of distilled water. The mixture was stirred. Thereto was added 7.3 g of N,N'-bis(2-hydroxyethyl)-1,2-diaminoethane prepared in Example 27, and then was added 250 ml of 1,4-dioxane. 13.4 g of palmitoyl chloride was gradually added dropwise to the resulting mixture for 1 hour under violent stirring at 10° C. After stirring for 2 hours at 10° C., 14.7 g of oleoyl chloride was gradually added dropwise thereto for 1 hour. After stirring for 2 hours, the mixture was filtered, and then the filtrate was mixed with 200 ml of chloroform, and washed twice with 200 ml of distilled water. The organic phase was cooled to produce solid material, which was recovered by filtration. The solid material was dried and recrystallized from acetone, to give 26.5 g of the title compound as white powder, which was identified by IR and NMR. The results are shown in Table 3.

EXAMPLE 31

Preparation of 1,2-bis(N-(3-hydroxypropyl)-palmitoylamino)ethane

The procedure described in Example 27 was followed by employing 60.1 g of 3-aminopropanol, instead of ethanolamine of Example 27, to give 13.2 g of N,N'-bis(3-hydroxypropyl)-1,2-diaminoethane.

Subsequently, the procedure described in Example 27 was followed by employing 8.8 g of N,N'-bis(3-hydroxypropyl)-1,2-diaminoethane prepared above, to give 23.7 g of the title compound as white powder, which was identified by IR and NMR. The results are shown in Table 3.

EXAMPLE 32

Preparation of 1,2-bis(N-(4-hydroxybutyl)-palmitoylamino) ethane

The procedure described in Example 27 was followed by employing 71.3 g of 4-aminobutanol, instead of ethanolamine of Example 27, to give 10.5 g of N,N'-bis(4-hydroxybutyl)-1,2-diaminoethane.

Subsequently, the procedure described in Example 27 was followed by employing 9.9 g of N,N'-bis(4-hydroxybutyl)-1,2-diaminoethane prepared above, to give 25.3 g of the title compound as white powder, which was identified by IR and NMR. The results are shown in Table 3.

EXAMPLE 33

Preparation of 1,3-bis(N-(2-hydroxyethyl)-palmitoylamino) propane

The procedure described in Example 27 was followed by employing 18.8 g of 1,3-dibromopropane, instead of 1,2-dibromoethane of Example 27, to give 13.8 g of N,N'-bis(2-hydroxyethyl)-1,3-diaminopropane.

Subsequently, the procedure described in Example 27 was followed by employing 7.6 g of N,N'-bis(2-hydroxyethyl)-1,3-diaminopropane prepared above, to give 23.1 g of the title compound as white powder, which was identified by IR and NMR. The results are shown in Table 3.

EXAMPLE 34

Preparation of 1,3-bis(N-(2-hydroxyethyl)-oleoylamino) propane

The procedure described in Example 33 was followed by employing 7.3 g of N,N'-bis(2-hydroxyethyl)-1,3-diaminopropane prepared in Example 33 and 20.9 g of oleoyl chloride, instead of palmitoyl chloride of Example 33, to give 26.7 g of the title compound as viscous oil, which was identified by IR and NMR. The results are shown in Table 3.

EXAMPLE 35

Preparation of 1,4-bis(N-(2-hydroxyethyl)-palmitoylamino) butane

The procedure described in Example 27 was followed by employing 60.1 g of ethanolamine and 18.8 g of 1,4-dibromobutane, instead of 1,2-dibromoethane of Example 27, to give 13.2 g of N,N'-bis(2-hydroxyethyl)-1,4-diaminobutane.

Subsequently, the procedure described in Example 27 was followed by employing 8.8 g of N,N'-bis(2-hydroxyethyl)-1,4-diaminobutane prepared above, to give 23.0 g of the title compound as white powder, which was identified by IR and NMR. The results are shown in Table 3.

TABLE 3

| Compounds | | $^1$H-NMR ($\delta$, ppm) | IR (cm$^{-1}$; C=O) | $^{13}$C-NMR (ppm; C=O) |
|---|---|---|---|---|
| Ex. | 27 | 0.9(6H, t), 1.2(48H, s), 1.5(4H, m), 2.3(4H, m), 3.2(8H, m), 3.5(4H, m) | 1620 | 171 |
| | 28 | 0.9(6H, t), 1.2(32H, s), 1.5(4H, m), 2.3(4H, m), 3.2(8H, m), 3.6(4H, m) | 1630 | 172 |
| | 29 | 0.9(6H, t), 1.2(40H, s), 1.6(4H, m), 2.0(8H, m), 2.3(4H, m), 3.2(8H, m), 3.6(4H, m), 5.3(4H, m) | 1625 | 172 |
| | 30 | 0.9(6H, t), 1.2(44H, s), 1.6(8H, m), 2.0(4H, m), 2.3(4H, m), 3.4(4H, m), 3.6(4H, m), 5.3(2H, m) | 1625 | 171 |
| | 31 | 0.9(6H, t), 1.2(48H, s), 1.6(8H, m), 2.3(4H, m), 3.2(8H, m), 3.6(4H, m) | 1630 | 172 |
| | 32 | 0.9(6H, t), 1.2(48H, s), 1.6(12H, m), 2.3(4H, m), | 1630 | 172 |

TABLE 3-continued

| Compounds | $^1$H-NMR (δ, ppm) | IR (cm$^{-1}$; C=O) | $^{13}$C-NMR (ppm; C=O) |
|---|---|---|---|
| | 3.2(8H, m), 3.6(4H, m) | | |
| 33 | 0.9(6H, t), 1.2(40H, s), 1.6(4H, m), 2.0(8H, m), 2.3(4H, m), 3.2(8H, m), 3.6(4H, m), 5.3(4H, m) | 1625 | 172 |
| 34 | 0.9(6H, t), 1.2(42H, s), 1.6(4H, m), 2.0(8H, m), 2.3(4H, m), 3.2(8H, m), 3.6(4H, m), 5.3(4H, m) | 1630 | 172 |
| 35 | 0.9(6H, t), 1.2(48H, s), 1.6(8H, m), 2.3(4H, m), 3.2(8H, m), 3.6(4H, m) | 1630 | 172 |

EXAMPLE 36
Preparation of 1,3-bis(N-(2-hydroxyethyl)-palmitoylamino)-2-hydroxypropane The procedure described in Example 27 was followed by employing 12.9 g of 1,3-dichloro-2-hydroxypropane, instead of 1,2-dibromoethane of Example 27, to give 13.1 g of N,N'-bis(2-hydroxyethyl)-2-hydroxy-1,3-propanediamine.

Subsequently, into a 500 ml rounded-flask, were introduced 4.0 g of magnesium oxide and 80 g of distilled water. The mixture was stirred, and was added 8.9 g of N,N'-bis(2-hydroxyethyl)-2-hydroxy-1,3-propanediamine prepared above, and then was added 250 ml of 1,4-dioxane. 26.8 g of palmitoyl chloride was gradually added dropwise to the resulting mixture for 1 hour under violent stirring at a room temperature. After stirring for 2 hours, the mixture was filtered, and then the filtrate was mixed with 200 ml of chloroform, and washed twice with 200 ml of distilled water. The organic phase was seperated; on cooling a precipitated, which was collected and recrystallized from acetone, to give 24.3 g of the title compound as white powder, which was identified by IR and NMR. The results are shown in Table 4.

EXAMPLE 37
Preparation of 1,3-bis(N-(2-hydroxyethyl)-lauroylamino)-2-hydroxypropane This compound was prepared according to the procedure of Example 36 using the 21.3 g of lauroyl chloride, to give 19.5 g of the title compound as white powder, which was identified by IR and NMR. The results are shown in Table 4.

EXAMPLE 38
Preparation of 1,3-bis(N-(2-hydroxyethyl)-oleoylamino)-2-hydroxypropane This compound was prepared according to the procedure of Example 36 using the 29.3 g of oleoyl chloride, to give 19.5 g of the title compound as yellowish oil, which was identified by IR and NMR. The results are shown in Table 4.

EXAMPLE 39
Preparation of N,N'-bis(3-hydroxypropyl)-N-palmitoyl-N'-oleoyl-1,3-diamino-2-hydroxypropane Into a 500 ml two-necked flask equipped with reflux condenser, 59.0 g of 3-amino-1-propanol and 200 ml of ethanol were placed. While violently stirring, 9.3 g of epichlorohydrin was added dropwise over 1 hours. After the addition was complete, the mixture was refluxed for 4 hours. The reaction mixture was cooled to a room temperature, the solution of KOH/ethanol was added to produce solid precipitates, which were removed by filtration. The solvent and unreacted 3-amino-1-propanol were evaporated off under reduced pressure and then was recrystallized from ethanol and chloroform. The product was filtered and dried under reduced pressure to give 18.2 g of N,N'-bis(3-hydroxypropyl)-2-hydroxy-1,3-propanediamine.

Into other 500 ml rounded-flask, 4.0 g of magnesium oxide and 80 g of distilled water were placed. While stirring resultant mixture, 10.4 g of N,N'-bis(3-hydroxypropyl)-2-hydroxy-1,3-propanediamine was added, and then was added 250 ml of 1,4-dioxane. 13.4 g of palmitoyl chloride was added portionwise to the resulting mixture over 1 hour under violent stirring at a room temperature. After stirring for 2 hours at 10° C., 14.7 g of oleoyl chloride was gradually added dropwise over 1 hour. After stirring again for 2 hours, the mixture was filtered, and then the filtrate was mixed with 200 ml of chloroform and washed twice with 200 ml of distilled water. The organic phase was cooled to produce solid material, which was recovered by filtration. The solid material was dried and recrystallized from acetone to give 26.5 g of the title compound as white powder, which was identified by IR and NMR. The results are shown in Table 4.

EXAMPLE 40
Preparation of phosphate diester of 1,3-bis(N-(2-hydroxyethyl)-palmitoylamino)-2-hydroxypropane Into 250 ml three necked-flask, 24.0 g of 1,3-bis(N-(2-hydroxyethyl)-palmitoylamino)-2-hydroxypropane and 100 ml of 1,2-dichloroethane were placed under stirring to be dissolved. The mixture was cooled to 10~15° C. in an ice bath, added dropwise the solution of 17 g of phosphorus oxychloride in 25 ml of 1,2-dichloroethane, the temperature of the solution was kept at 10~15° C.

After the addition, the mixture was stirred for 1~2 hours. 100 ml of distilled water was added, and stirred violently. The organic phase was seperated and washed with each 100 ml of distilled water twice. The organic phase was dried over magnesium sulfate, and then the solvent was evaporated off under reduced pressure. The product was recrystallized from acetonitrile to give 29 g of the title compound, which was identified by IR and NMR. The results are shown in Table 4.

EXAMPLE 41
Preparation of phosphate diester of 1,3-bis(N-(2-hydroxyethyl)-lauroylamino)-2-hydroxypropane This compound was prepared according to the procedure of Example 40 using the 18.0 g of 1,3-bis(N-(2-hydroxyethyl)-lauroylamino)-2-hydroxy-propane and 12 g of phosphorous oxychloride. The yield of title compound was 22 g, which was identified by IR and NMR. The results are shown in Table 4.

EXAMPLE 42
Preparation of phosphate diester of 1,3-bis(N-(2-hydroxyethyl)-oleoylamino)-2-hydroxypropane This compound was prepared according to the procedure of Example 40 using the 26.0 g of 1,3-bis(N-(2-hydroxyethyl)-oleoylamino)-2-hydroxypropane and 12 g of 11.5 g of phosphorus oxychloride. The yield of title compound was 30 g, which was identified by IR and NMR. The results are shown in Table 4.

EXAMPLE 43
Preparation of sulfate diester of N,N'-bis(3-hydroxypropyl)-N-palmitoyl-N'-oleoyl-1,3-diamino-2-hydroxypropane This compound was prepared according to the procedure of Example 40 using the 18.0 g of 25.0 g of N,N'-bis(3-hydroxypropyl)-N-palmitoyl-N'-oleoyl-1,3-diamino-2-hydroxypropane and 9 g of chlorosulfonic acid. The yield of title compound was 30 g, which was identified by IR and NMR. The results are shown in Table 4.

EXAMPLE 44
Preparation of phosphate diester of 1,2-bis(N-(2-hydroxyethyl)-palmitoylamino)ethane This compound was prepared according to the procedure of Example 40 using the 20.0 g of 1,2-bis(N-(2-hydroxyethyl)-palmitoylamino)ethane and 12 g of 10.0 g of phosphorus oxychloride. The yield of title compound was 23.5 g, which was identified by IR and NMR. The results are shown in Table 4.

TABLE 4

| Compounds | | $^1$H-NMR ($\delta$, ppm) | IR (cm$^{-1}$; C=O) | $^{13}$C-NMR (ppm; C=O) |
|---|---|---|---|---|
| Ex. | 36 | 0.9(6H, t), 1.2(48H, s), 1.5(4H, m), 2.3(4H, m), 3.2(4H, m), 3.5(4H, m), 3.6(4H, m), 4.0(1H, m) | 1620 | 172 |
| | 37 | 0.9(6H, t), 1.2(32H, s), 1.5(4H, m), 2.3(4H, m), 3.2(4H, m), 3.5(4H, m), 3.6(4H, m), 4.0(1H, m) | 1623 | 170 |
| | 38 | 0.9(6H, t), 1.2(40H, s), 1.6(4H, m), 2.0(8H, m), 2.3(4H, t), 3.2(4H, m), 3.5(4H, m), 3.6(4H, m), 4.0(1H, m), 5.3(4H, m) | 1620 | 171 |
| | 39 | 0.9(6H, m), 1.2(44H, s), 1.6(8H, m), 2.0(4H, m), 2.3(4H, t), 3.0(4H, m), 3.4(4H, m), 3.6(4H, m), 3.9(1H, m), 5.3(2H, m) | 1625 | 172 |
| | 40 | 0.9(6H, t), 1.3(48H, s), 1.6(4H, m), 2.4(4H, m), 3.4(4H, m), 3.6(4H, m), 3.9(4H, m), 4.5(1H, m) | 1618 | 171 |
| | 41 | 0.9(6H, t), 1.3(32H, s), 1.6(4H, m), 2.4(4H, m), 3.4(4H, m), 3.6(4H, m), 4.0(4H, m), 4.6(1H, m) | 1620 | 170 |
| | 42 | 0.9(6H, t), 1.3(40H, s), 1.6(4H, m), 2.1(8H, m), 2.4(4H, t), 3.4(4H, m), 3.6(4H, m), 4.0(4H, m), 4.5(1H, m), 5.3(4H, m) | 1617 | 172 |
| | 43 | 0.9(6H, m), 1.3(44H, s), 1.6(8H, m), 2.0(4H, m), 2.4(4H, t), 3.4(4H, m), 3.6(4H, m), 4.0(4H, m), 4.5(1H, m), 5.3(2H, m) | 1622 | 173 |
| | 44 | 0.9(6H, t), 1.3(48H, s), 1.6(4H, m), 2.3(4H, m), 3.4(8H, m), 3.9(4H, m) | 1625 | 172 |

EXAMPLES 45~49
Preparation of salts of compounds of Examples 40 to 44

Each compounds prepared in Examples 40 to 44 was dissolved in ethanol, and then ethanol solution containing NaOH in an equivalent concentration corresponding to phosphoric group or sulfuric group contained in the compound was added under stirring. After neutralization, the resulting salts were filtered and dried.

EXPERIMENTAL EXAMPLE 1
The Solubility of a Natural Ceramide and of Ceramide-like Compounds Among 6 types of the natural ceramides represented by the Formulae 3 to 9, ceramide Type 3 represented by the Formula 5 has been mainly used in the cosmetics. Accordingly, in this experiment, were compared solubilities of the ceramide Type 3 (obtained from bovine brain) and the ceramide-like compounds prepared in various solvents such as ethanol, which have been widely used in the cosmetics. Samples were dissolved in the solvents of 8° C. and then cooled to 20° C. The results are shown in Table 5.

TABLE 5

Solubility of the natural ceramide and the ceramide-like compounds in various solvents (wt/wt %, 20° C.)

| Comounds | Solvents | | | | |
|---|---|---|---|---|---|
| | Ethanol | Octyl dodecanol | Octyl palmitate | Isopropyl palmitate | Cetyl octanoate |
| Natural ceramide (Formula 5) | <1% | <1% | <1% | <1% | <1% |
| Example 27 | >5% | >5% | >5% | >5% | >5% |
| Example 36 | >5% | >5% | >5% | >5% | >5% |
| Example 37 | >5% | >5% | >5% | >5% | >5% |
| Example 38 | >7.5% | >10% | >10% | >10% | >10% |
| Example 39 | >5% | >7.5% | >5% | >5% | >7.5% |
| Example 40 | >10% | >3% | >5% | >5% | >5% |

TABLE 5-continued

Solubility of the natural ceramide and the ceramide-like compounds in various solvents (wt/wt %, 20° C.)

| Comounds | Solvents | | | | |
|---|---|---|---|---|---|
| | Ethanol | Octyl dodecanol | Octyl palmitate | Isopropyl palmitate | Cetyl octanoate |
| Example 41 | >10% | >5% | >5% | >5% | >5% |
| Example 42 | >20% | >5% | >5% | >7.5% | >7.5% |
| Example 43 | >15% | >5% | >5% | >5% | >5% |
| Example 44 | >10% | >3% | >5% | >5% | >7.5% |

In this experiment, approximately, 0.5% of the natural ceramide was a gelled suspension where is no fluidity in all the solvents.

<Formulations 1~4 and Comparative Formulations 1~2>
Cream

| Materials | C. Formulations 1 | C. Formulations 2 | Formulations 1 | Formulations 2 | Formulations 3 | Formulations 4 |
|---|---|---|---|---|---|---|
| Cetostearyl alcohol | 1.0 | 1.0 | 1.0 | 1.0 | 1.0 | 1.0 |
| Lipophilic monostearic glycerine | 1.0 | 1.0 | 1.0 | 1.0 | 1.0 | 1.0 |
| Monostearic polyoxyethylene glycerine | 1.5 | 1.5 | 1.5 | 1.5 | 1.5 | 1.5 |
| Self-emulsified monostearic glycerine | 1.0 | 1.0 | 1.0 | 1.0 | 1.0 | 1.0 |
| Caprylic/capric triglyceride | 6.0 | 6.0 | 6.0 | 6.0 | 6.0 | 6.0 |
| Liquid paraffin | 6.0 | 6.0 | 6.0 | 6.0 | 6.0 | 6.0 |
| Squalane | 4.0 | 4.0 | 4.0 | 4.0 | 4.0 | 4.0 |
| Tocopheryl acetate | 0.5 | 0.5 | 0.5 | 0.5 | 0.5 | 0.5 |
| Natural ceramide of Type 3 | — | 1.0 | — | — | — | — |
| Compound of Example 4 | — | — | 1.0 | — | — | — |
| Compound of Example 5 | — | — | — | 1.0 | — | — |
| Compound of Example 6 | — | — | — | — | 1.0 | — |
| Compound of Example 7 | — | — | — | — | — | 1.0 |
| Stearic acid | 0.5 | 0.5 | 0.5 | 0.5 | 0.5 | 0.5 |
| Cholesterol | 0.7 | 0.7 | 0.7 | 0.7 | 0.7 | 0.7 |
| Alantoin | 0.4 | 0.4 | 0.4 | 0.4 | 0.4 | 0.4 |
| Glycine | 0.5 | 0.5 | 0.5 | 0.5 | 0.5 | 0.5 |
| Glycerine | 7.0 | 7.0 | 7.0 | 7.0 | 7.0 | 7.0 |
| 1,3-Butyleneglycol | 7.0 | 7.0 | 7.0 | 7.0 | 7.0 | 7.0 |
| Xantan gum | 0.5 | 0.5 | 0.5 | 0.5 | 0.5 | 0.5 |
| Placenta extracts | 1.0 | 1.0 | 1.0 | 1.0 | 1.0 | 1.0 |
| Hyanuronic acid extracts | 1.0 | 1.0 | 1.0 | 1.0 | 1.0 | 1.0 |
| Green tea extracts | 1.0 | 1.0 | 1.0 | 1.0 | 1.0 | 1.0 |
| Preservative | q.s. | q.s. | q.s. | q.s. | q.s. | q.s. |
| Perfume | q.s. | q.s. | q.s. | q.s. | q.s. | q.s. |
| Distilled water | to 100 | to 100 | to 100 | to 100 | to 100 | to 100 |

<Formulations 5~12>
Cream

| Materials | 5 | 6 | 7 | 8 | 9 | 10 | 11 | 12 |
|---|---|---|---|---|---|---|---|---|
| Cetostearyl alcohol | 1.0 | 1.0 | 1.0 | 1.0 | 1.0 | 1.0 | 1.0 | 1.0 |
| Lipophilic monostearic glycerine | 1.0 | 1.0 | 1.0 | 1.0 | 1.0 | 1.0 | 1.0 | 1.0 |
| Monostearic polyoxyethylene glycerine | 1.5 | 1.5 | 1.5 | 1.5 | 1.5 | 1.5 | 1.5 | 1.5 |
| Self-emulsified monostearic glycerine | 1.0 | 1.0 | 1.0 | 1.0 | 1.0 | 1.0 | 1.0 | 1.0 |
| Caprylic/capric triglyceride | 6.0 | 6.0 | 6.0 | 6.0 | 6.0 | 6.0 | 6.0 | 6.0 |
| Liquid paraffin | 6.0 | 6.0 | 6.0 | 6.0 | 6.0 | 6.0 | 6.0 | 6.0 |
| Squalane | 4.0 | 4.0 | 4.0 | 4.0 | 4.0 | 4.0 | 4.0 | 4.0 |
| Tocopheryl acetate | 0.5 | 0.5 | 0.5 | 0.5 | 0.5 | 0.5 | 0.5 | 0.5 |
| Natural ceramide of Type 3 | — | — | — | — | — | — | — | — |
| Compound of Example 8 | 1.0 | — | — | — | — | — | — | — |
| Compound of Example 9 | — | 1.0 | — | — | — | — | — | — |
| Compound of Example 10 | — | — | 1.0 | — | — | — | — | — |
| Compound of Example 11 | — | — | — | 1.0 | — | — | — | — |
| Compound of Example 27 | — | — | — | — | 1.0 | — | — | — |
| Compound of Example 28 | — | — | — | — | — | 1.0 | — | — |
| Compound of Example 29 | — | — | — | — | — | — | 1.0 | — |
| Compound of Example 30 | — | — | — | — | — | — | — | 1.0 |
| Stearic acid | 0.5 | 0.5 | 0.5 | 0.5 | 0.5 | 0.5 | 0.5 | 0.5 |
| Cholesterol | 0.7 | 0.7 | 0.7 | 0.7 | 0.7 | 0.7 | 0.7 | 0.7 |
| Alantoin | 0.4 | 0.4 | 0.4 | 0.4 | 0.4 | 0.4 | 0.4 | 0.4 |
| Glycine | 0.5 | 0.5 | 0.5 | 0.5 | 0.5 | 0.5 | 0.5 | 0.5 |
| Glycerine | 7.0 | 7.0 | 7.0 | 7.0 | 7.0 | 7.0 | 7.0 | 7.0 |
| 1,3-Butyleneglycol | 7.0 | 7.0 | 7.0 | 7.0 | 7.0 | 7.0 | 7.0 | 7.0 |
| Xantan gum | 0.5 | 0.5 | 0.5 | 0.5 | 0.5 | 0.5 | 0.5 | 0.5 |
| Placenta extracts | 1.0 | 1.0 | 1.0 | 1.0 | 1.0 | 1.0 | 1.0 | 1.0 |
| Hyanuronic acid extracts | 1.0 | 1.0 | 1.0 | 1.0 | 1.0 | 1.0 | 1.0 | 1.0 |
| Green tea extracts | 1.0 | 1.0 | 1.0 | 1.0 | 1.0 | 1.0 | 1.0 | 1.0 |
| Preservative | q.s. | q.s. | q.s. | q.s. | q.s. | q.s. | q.s. | q.s. |
| Perfume | q.s. | q.s. | q.s. | q.s. | q.s. | q.s. | q.s. | q.s. |
| Distilled water | to 100 | to 100 | to 100 | to 100 | to 100 | to 100 | to 100 | to 100 |

<Formulations 13~21>
Cream

| Materials | 13 | 14 | 15 | 16 | 17 |
|---|---|---|---|---|---|
| Cetostearyl alcohol | 1.0 | 1.0 | 1.0 | 1.0 | 1.0 |
| Lipophilic monostearic glycerine | 1.0 | 1.0 | 1.0 | 1.0 | 1.0 |
| Monostearic polyoxyethylene glycerine | 1.5 | 1.5 | 1.5 | 1.5 | 1.5 |
| Self-emulsified monostearic glycerine | 1.0 | 1.0 | 1.0 | 1.0 | 1.0 |
| Caprylic/capric triglyceride | 6.0 | 6.0 | 6.0 | 6.0 | 6.0 |
| Liquid paraffin | 6.0 | 6.0 | 6.0 | 6.0 | 6.0 |
| Squalane | 4.0 | 4.0 | 4.0 | 4.0 | 4.0 |
| Tocopheryl acetate | 0.5 | 0.5 | 0.5 | 0.5 | 0.5 |
| Natural ceramide of Type 3 | — | — | — | — | — |
| Compound of Example 31 | 1.0 | — | — | — | — |
| Compound of Example 32 | — | 1.0 | — | — | — |
| Compound of Example 33 | — | — | 1.0 | — | — |
| Compound of Example 34 | — | — | — | 1.0 | — |
| Compound of Example 35 | — | — | — | — | 1.0 |
| Compound of Example 36 | — | — | — | — | — |
| Compound of Example 37 | — | — | — | — | — |
| Compound of Example 38 | — | — | — | — | — |
| Compound of Example 39 | — | — | — | — | — |
| Stearic acid | 0.5 | 0.5 | 0.5 | 0.5 | 0.5 |

-continued

| Materials | | | | | |
|---|---|---|---|---|---|
| Cholesterol | 0.7 | 0.7 | 0.7 | 0.7 | 0.7 |
| Alantoin | 0.4 | 0.4 | 0.4 | 0.4 | 0.4 |
| Glycine | 0.5 | 0.5 | 0.5 | 0.5 | 0.5 |
| Glycerine | 7.0 | 7.0 | 7.0 | 7.0 | 7.0 |
| 1,3-Butyleneglycol | 7.0 | 7.0 | 7.0 | 7.0 | 7.0 |
| Xantan gum | 0.5 | 0.5 | 0.5 | 0.5 | 0.5 |
| Placenta extracts | 1.0 | 1.0 | 1.0 | 1.0 | 1.0 |
| Hyanuronic acid extracts | 1.0 | 1.0 | 1.0 | 1.0 | 1.0 |
| Green tea extracts | 1.0 | 1.0 | 1.0 | 1.0 | 1.0 |
| Preservative | q.s. | q.s. | q.s. | q.s. | q.s. |
| Perfume | q.s. | q.s. | q.s. | q.s. | q.s. |
| Distilled water | to 100 | to 100 | to 100 | to 100 | to 100 |

| | Formulations | | | |
|---|---|---|---|---|
| Materials | 18 | 19 | 20 | 21 |
| Cetostearyl alcohol | 1.0 | 1.0 | 1.0 | 1.0 |
| Lipophilic monostearic glycerine | 1.0 | 1.0 | 1.0 | 1.0 |
| Monostearic polyoxyethylene glycerine | 1.5 | 1.5 | 1.5 | 1.5 |
| Self-emulsified monostearic glycerine | 1.0 | 1.0 | 1.0 | 1.0 |
| Caprylic/capric triglyceride | 6.0 | 6.0 | 6.0 | 6.0 |
| Liquid paraffin | 6.0 | 6.0 | 6.0 | 6.0 |
| Squalane | 4.0 | 4.0 | 4.0 | 4.0 |
| Tocopheryl acetate | 0.5 | 0.5 | 0.5 | 0.5 |
| Natural ceramide of Type 3 | — | — | — | — |
| Compound of Example 31 | — | — | — | — |
| Compound of Example 32 | — | — | — | — |
| Compound of Example 33 | — | — | — | — |
| Compound of Example 34 | — | — | — | — |
| Compound of Example 35 | — | — | — | — |
| Compound of Example 36 | 1.0 | — | — | — |
| Compound of Example 37 | — | 1.0 | — | — |
| Compound of Example 38 | — | — | 1.0 | — |
| Compound of Example 39 | — | — | — | 1.0 |
| Stearic acid | 0.5 | 0.5 | 0.5 | 0.5 |
| Cholesterol | 0.7 | 0.7 | 0.7 | 0.7 |
| Alantoin | 0.4 | 0.4 | 0.4 | 0.4 |
| Glycine | 0.5 | 0.5 | 0.5 | 0.5 |
| Glycerine | 7.0 | 7.0 | 7.0 | 7.0 |
| 1,3-Butyleneglycol | 7.0 | 7.0 | 7.0 | 7.0 |
| Xantan gum | 0.5 | 0.5 | 0.5 | 0.5 |
| Placenta extracts | 1.0 | 1.0 | 1.0 | 1.0 |
| Hyanuronic acid extracts | 1.0 | 1.0 | 1.0 | 1.0 |
| Green tea extracts | 1.0 | 1.0 | 1.0 | 1.0 |
| Preservative | q.s. | q.s. | q.s. | q.s. |
| Perfume | q.s. | q.s. | q.s. | q.s. |
| Distilled water | to 100 | to 100 | to 100 | to 100 |

<Formulations 22~31>
Cream

| | Formulations | | | | |
|---|---|---|---|---|---|
| Materials | 22 | 23 | 24 | 25 | 26 |
| Cetostearyl alcohol | 1.0 | 1.0 | 1.0 | 1.0 | 1.0 |
| Lipophilic monostearic glycerine | 1.0 | 1.0 | 1.0 | 1.0 | 1.0 |
| Monostearic polyoxyethylene glycerine | 1.5 | 1.5 | 1.5 | 1.5 | 1.5 |
| Self-emulsified monostearic glycerine | 1.0 | 1.0 | 1.0 | 1.0 | 1.0 |
| Caprylic/capric triglyceride | 6.0 | 6.0 | 6.0 | 6.0 | 6.0 |
| Liquid paraffin | 6.0 | 6.0 | 6.0 | 6.0 | 6.0 |
| Squalane | 4.0 | 4.0 | 4.0 | 4.0 | 4.0 |
| Tocopheryl acetate | 0.5 | 0.5 | 0.5 | 0.5 | 0.5 |
| Natural ceramide of Type 3 | — | — | — | — | — |
| Compound of Example 22 | 1.0 | — | — | — | — |
| Compound of Example 23 | — | 1.0 | — | — | — |
| Compound of Example 24 | — | — | 1.0 | — | — |
| Compound of Example 25 | — | — | — | 1.0 | — |
| Compound of Example 26 | — | — | — | — | 1.0 |
| Compound of Example 45 | — | — | — | — | — |
| Compound of Example 46 | — | — | — | — | — |
| Compound of Example 47 | — | — | — | — | — |
| Compound of Example 48 | — | — | — | — | — |
| Compound of Example 49 | — | — | — | — | — |
| Stearic acid | 0.5 | 0.5 | 0.5 | 0.5 | 0.5 |
| Cholesterol | 0.7 | 0.7 | 0.7 | 0.7 | 0.7 |
| Alantoin | 0.4 | 0.4 | 0.4 | 0.4 | 0.4 |
| Glycine | 0.5 | 0.5 | 0.5 | 0.5 | 0.5 |
| Glycerine | 7.0 | 7.0 | 7.0 | 7.0 | 7.0 |
| 1,3-Butyleneglycol | 7.0 | 7.0 | 7.0 | 7.0 | 7.0 |
| Xantan gum | 0.5 | 0.5 | 0.5 | 0.5 | 0.5 |
| Placenta extracts | 1.0 | 1.0 | 1.0 | 1.0 | 1.0 |
| Hyanuronic acid extracts | 1.0 | 1.0 | 1.0 | 1.0 | 1.0 |
| Green tea extracts | 1.0 | 1.0 | 1.0 | 1.0 | 1.0 |
| Preservative | q.s. | q.s. | q.s. | q.s. | q.s. |
| Perfume | q.s. | q.s. | q.s. | q.s. | q.s. |
| Distilled water | to 100 | to 100 | to 100 | to 100 | to 100 |

| | Formulations | | | | |
|---|---|---|---|---|---|
| Materials | 27 | 28 | 29 | 30 | 31 |
| Cetostearyl alcohol | 1.0 | 1.0 | 1.0 | 1.0 | 1.0 |
| Lipophilic monostearic glycerine | 1.0 | 1.0 | 1.0 | 1.0 | 1.0 |
| Monostearic polyoxyethylene glycerine | 1.5 | 1.5 | 1.5 | 1.5 | 1.5 |
| Self-emulsified monostearic glycerine | 1.0 | 1.0 | 1.0 | 1.0 | 1.0 |
| Caprylic/capric triglyceride | 6.0 | 6.0 | 6.0 | 6.0 | 6.0 |
| Liquid paraffin | 6.0 | 6.0 | 6.0 | 6.0 | 6.0 |
| Squalane | 4.0 | 4.0 | 4.0 | 4.0 | 4.0 |
| Tocopheryl acetate | 0.5 | 0.5 | 0.5 | 0.5 | 0.5 |
| Natural ceramide of Type 3 | — | — | — | — | — |
| Compound of Example 22 | — | — | — | — | — |
| Compound of Example 23 | — | — | — | — | — |
| Compound of Example 24 | — | — | — | — | — |
| Compound of Example 25 | — | — | — | — | — |
| Compound of Example 26 | — | — | — | — | — |
| Compound of Example 45 | 1.0 | — | — | — | — |
| Compound of Example 46 | — | 1.0 | — | — | — |
| Compound of Example 47 | — | — | 1.0 | — | — |
| Compound of Example 48 | — | — | — | 1.0 | — |
| Compound of Example | — | — | — | — | 1.0 |

-continued

| 49 | | | | | |
|---|---|---|---|---|---|
| Stearic acid | 0.5 | 0.5 | 0.5 | 0.5 | 0.5 |
| Cholesterol | 0.7 | 0.7 | 0.7 | 0.7 | 0.7 |
| Alantoin | 0.4 | 0.4 | 0.4 | 0.4 | 0.4 |
| Glycine | 0.5 | 0.5 | 0.5 | 0.5 | 0.5 |
| Glycerine | 7.0 | 7.0 | 7.0 | 7.0 | 7.0 |
| 1,3-Butyleneglycol | 7.0 | 7.0 | 7.0 | 7.0 | 7.0 |
| Xantan gum | 0.5 | 0.5 | 0.5 | 0.5 | 0.5 |
| Placenta extracts | 1.0 | 1.0 | 1.0 | 1.0 | 1.0 |
| Hyanuronic acid extracts | 1.0 | 1.0 | 1.0 | 1.0 | 1.0 |
| Green tea extracts | 1.0 | 1.0 | 1.0 | 1.0 | 1.0 |
| Preservative | q.s. | q.s. | q.s. | q.s. | q.s. |
| Perfume | q.s. | q.s. | q.s. | q.s. | q.s. |
| Distilled water | to 100 | to 100 | to 100 | to 100 | to 100 |

EXPERIMENTAL EXAMPLE 2

Human Patch Test: Safety Onto the Skin

In order to evaluate the safety of the cosmetic compositions containing the ceramide-like compounds onto the skin, the conventional patch test was carried out for eleven(11) groups consisting of ten(10) of healthy females aging 26~45 years, and the level of skin irritation was estimated according to the following scoring system:

| | |
|---|---|
| 4 | Extremely severe irritation, estimated to be inadequate as a cosmetic |
| 3 | Severe irritation, estimated to be better not to use as a cosmetic |
| 2 | A little irritation, estimated to be carefully used as a cosmetic |
| 1 | Little irritation |
| 0 | No irritation, estimated to be adequate for the sensitive skin |

The scores of Table 6 are average for ten(10) scores.

TABLE 6

| | C. Formulations | | Formulations | | | | | | | | | |
|---|---|---|---|---|---|---|---|---|---|---|---|---|
| Material | 1 | 2 | 9 | 18 | 19 | 20 | 21 | 27 | 28 | 29 | 30 | 31 |
| Scores | 0.3 | 0.3 | 0.2 | 0.2 | 0.2 | 0.3 | 0.2 | 0.2 | 0.3 | 0.3 | 0.3 | 0.2 |

As shown in Table 6, there is no significant difference in skin irritation, compared with control. Therefore, it is estimated that the ceramide-like compounds of the present invention are a safe material for topical application on the skin.

EXPERIMENTAL EXAMPLE 3

Skin Recuperation

In order to evaluate the skin recuperation of the cosmetic compositions containing the ceramide-like compounds, 2.5% of SDS(sodium dodecylsulfate) or acetone was used as an irritant and compositions prepared in Formulations and Comparative Formulations were used as a curative material. And, skin irritation and its recuperation was evaluated by measuring TEWL(transepidermal water loss) with Evaporimeter.

(3-1) Test for Compositions of Formulations 1~4 and C. Formulations 1~2

The test was carried out for 6 groups consisting of five(5) of hairless guinea pigs. The pig's rib was treated with 2.5% of SDS for 30 minutes using Finn chamber. After removing the SDS patch, 200 μl of each test material of the composition prepared in Formulations or Comparative Formulations was applied to human skin immediately after barrier disruption.

Measurement of TEWL was carried before treatment, 30 min, 1 hour, 2 hours, 4 hours, 7 hours and 24 hours after SDS treatment. The results are shown in Table 7. The score is calculated by considering TEWL measured before SDS treatment as "10". Each score of Table 7 is average for five(5) scores.

TABLE 7

| | | Before | After removing SDS patch | | | | | Unit: AU |
|---|---|---|---|---|---|---|---|---|
| | | SDS patch | 30 min | 1 hour | 2 hours | 4 hours | 7 hours | 24 hours |
| C. Formulation | 1 | 10 | 30 | 32 | 27 | 24 | 20 | 17 |
| | 2 | 10 | 27 | 29 | 20 | 15 | 13 | 12 |
| Formulation | 1 | 10 | 27 | 29 | 18 | 14 | 13 | 12 |
| | 2 | 10 | 28 | 30 | 20 | 16 | 14 | 12 |
| | 3 | 10 | 28 | 29 | 20 | 15 | 14 | 12 |
| | 4 | 10 | 29 | 30 | 19 | 16 | 13 | 12 |

(3-2) Test for Compositions of Formulations 5~12

The test was carried out for 8 groups consisting of five(5) of hairless guinea pigs, in the same procedure described in (3-1) test. The results are show in Table 8.

TABLE 8

| | | Before | After removing SDS patch | | | | | Unit: AU |
|---|---|---|---|---|---|---|---|---|
| | | SDS patch | 30 min | 1 hour | 2 hours | 4 hours | 7 hours | 24 hours |
| Formulation | 5 | 10 | 28 | 29 | 19 | 15 | 13 | 13 |
| | 6 | 10 | 28 | 30 | 20 | 16 | 14 | 12 |
| | 7 | 10 | 28 | 29 | 20 | 15 | 14 | 13 |
| | 8 | 10 | 29 | 30 | 19 | 16 | 15 | 13 |
| | 9 | 10 | 28 | 29 | 19 | 14 | 13 | 11 |
| | 10 | 10 | 27 | 30 | 21 | 16 | 14 | 12 |
| | 11 | 10 | 28 | 29 | 20 | 15 | 13 | 11 |
| | 12 | 10 | 28 | 30 | 19 | 15 | 13 | 12 |

(3-3) Test for Compositions of Formulations 13~21

The test was carried out for 9 groups consisting of five(5) of hairless guinea pigs, in the same procedure described in (3-1) test. The results are shown in Table 9.

TABLE 9

| | | Before | After removing SDS patch | | | | | Unit: AU |
|---|---|---|---|---|---|---|---|---|
| | | SDS patch | 30 min | 1 hour | 2 hours | 4 hours | 7 hours | 24 hours |
| Formulation | 13 | 10 | 28 | 30 | 20 | 15 | 14 | 12 |
| | 14 | 10 | 28 | 29 | 19 | 14 | 13 | 11 |
| | 15 | 10 | 27 | 30 | 21 | 16 | 14 | 12 |
| | 16 | 10 | 28 | 29 | 20 | 15 | 13 | 12 |
| | 17 | 10 | 28 | 30 | 19 | 15 | 13 | 12 |
| | 18 | 10 | 28 | 29 | 19 | 14 | 13 | 12 |
| | 19 | 10 | 27 | 30 | 21 | 16 | 14 | 13 |
| | 20 | 10 | 28 | 29 | 20 | 15 | 13 | 12 |
| | 21 | 10 | 28 | 30 | 19 | 15 | 13 | 12 |

(3-4) Test for Compositions of Formulations 22~26

The test was carried out for 5 groups consisting of five(5) of hairless guinea pigs, in the same procedure described in (3-1) test. The results are shown in Table 10.

TABLE 10

| | | Before SDS patch | After removing SDS patch | | | | | |
|---|---|---|---|---|---|---|---|---|
| | | | 30 min | 1 hour | 2 hours | 4 hours | 7 hours | 24 hours |
| Formulation | 22 | 10 | 28 | 27 | 20 | 15 | 13 | 12 |
| | 23 | 10 | 27 | 27 | 19 | 15 | 14 | 12 |
| | 24 | 10 | 28 | 26 | 20 | 16 | 14 | 12 |
| | 25 | 10 | 28 | 27 | 20 | 15 | 14 | 12 |
| | 26 | 10 | 29 | 27 | 20 | 15 | 13 | 12 |

Unit: AU (3-5) Test for Compositions of Formulations 27~31 and C. Formulations 1~2

The test was carried out for 7 groups consisting of five(5) of hairless guinea pigs. The pig's rib was treated with acetone for 30 minutes using Finn chamber. After removing the patch, 200 μl of each test material was applied on the patched position.

Skin irritation and its recuperation was evaluated by measuring TEWL through the stratum corneum with Evaporimeter. Measurement was carried before patch, 30 min, 1 hour, 2 hours, 4 hours, 6 hours and 8 hours after removing the patch. The results are shown in Table 11. The score is calculated by considering TEWL measured before acetone patch as "0" and TEWL measured immediately after removing the patch as "100". Each score of Table 11 is average for five(5) score.

TABLE 11

| | | Immediately after removing the patch | After removing the patch | | | | |
|---|---|---|---|---|---|---|---|
| | | | 30 min | 1 hour | 2 hours | 4 hours | 6 hours | 8 hours |
| C. Formulation | 1 | 100 | 98 | 95 | 92 | 82 | 80 | 77 |
| | 2 | 100 | 118 | 131 | 91 | 78 | 58 | 51 |
| Formulation | 27 | 100 | 98 | 95 | 61 | 51 | 40 | 32 |
| | 28 | 100 | 104 | 110 | 73 | 60 | 51 | 43 |
| | 29 | 100 | 99 | 97 | 61 | 52 | 40 | 30 |
| | 30 | 100 | 101 | 102 | 68 | 58 | 49 | 42 |
| | 31 | 100 | 97 | 92 | 65 | 53 | 41 | 33 |

Unit: AU

As shown in Tables 7 to 11, the compositions containing the ceramide-like compounds of the present invention are significantly effective in recuperation of the damaged stratum corneum. In particular, the recuperation proceeded quickly in the compositions containing the compounds having phosphoric group.

EXPERIMENTAL EXAMPLE 4
Protective Action Against Irriation

In order to evaluate the protecting action of the cosmetic compositions containing the ceramide-like compounds, 2.5% of SDS(sodium dodecylsulfate) was used as an irritant and compositions prepared in Examples and Comparative Examples were used as a protective material. And, the protective action was evaluated by measuring TEWL (transepidermal water loss) with Evaporimeter.

(4-1) Test for Compositions of Formulations 1~4 and C. Formulations 1~2

The test was carried out for 6 groups consisting of five(5) of hairless guinea pigs. The pig's rib was treated with the test material once a day for 7 days. And then, 2.5% of SDS was patched on the tested position for 30 minutes using Finn chamber.

Measurement of TEWL was carried before SDS treatment, 1 hour and 24 hours after SDS treatment. The results are shown in Table 12. The score is calculated by considering TEWL measured before SDS treatment as "10". Each score of Table 12 is average for five(5) score.

TABLE 12

| | | Before SDS patch | After removing SDS patch | |
|---|---|---|---|---|
| | | | 1 hour | 24 hours |
| C. Formulation | 1 | 10 | 24 | 15 |
| | 2 | 10 | 17 | 12 |
| Formulation | 1 | 10 | 16 | 11 |
| | 2 | 10 | 18 | 12 |
| | 3 | 10 | 17 | 12 |
| | 4 | 10 | 18 | 12 |

Unit: AU (4-2) Test for Compositions of Formulations 5~12

The test was carried out for 8 groups consisting of five(5) of hairless guinea pigs, in the same procedure described in (4-1) test. The results are shown in Table 13.

TABLE 13

| | | Before SDS patch | After removing SDS patch | |
|---|---|---|---|---|
| | | | 1 hour | 24 hours |
| Formulation | 5 | 10 | 16 | 11 |
| | 6 | 10 | 18 | 12 |
| | 7 | 10 | 17 | 12 |
| | 8 | 10 | 18 | 12 |
| | 9 | 10 | 16 | 12 |
| | 10 | 10 | 18 | 12 |
| | 11 | 10 | 17 | 12 |
| | 12 | 10 | 17 | 12 |

Unit: AU (4-3) Test for Compositions of Formulations 13~21

The test was carried out for 9 groups consisting of five(5) of hairless guinea pigs, in the same procedure described in (4-1) test. The results are shown in Table 14.

TABLE 14

| | | Before SDS patch | After removing SDS patch | |
|---|---|---|---|---|
| | | | 1 hour | 24 hours |
| Formulation | 13 | 10 | 17 | 15 |
| | 14 | 10 | 16 | 12 |
| | 15 | 10 | 18 | 12 |
| | 16 | 10 | 17 | 12 |
| | 17 | 10 | 17 | 12 |
| | 18 | 10 | 16 | 12 |
| | 19 | 10 | 18 | 12 |
| | 20 | 10 | 17 | 12 |
| | 21 | 10 | 17 | 12 |

Unit: AU (4-4) Test for Compositions of Formulations 22~31

The test was carried out for 10 groups consisting of five(5) of hairless guinea pigs, in the same procedure described in (4-1) test. The results are shown in Table 15.

TABLE 15

|  |  | Before SDS patch | After removing SDS patch | |
|---|---|---|---|---|
|  |  |  | 1 hour | 24 hours |
|  |  |  | Unit: AU | |
| Formulation | 22 | 10 | 16 | 12 |
|  | 23 | 10 | 18 | 12 |
|  | 24 | 10 | 17 | 12 |
|  | 25 | 10 | 16 | 12 |
|  | 26 | 10 | 17 | 12 |
|  | 27 | 10 | 15 | 11 |
|  | 28 | 10 | 16 | 12 |
|  | 29 | 10 | 14 | 11 |
|  | 30 | 10 | 17 | 12 |
|  | 31 | 10 | 14 | 11 |

As shown in Tables 12 to 15, compared with the composition containing no ceramide derivatives, the compositions containing the ceramide-like compounds of the present invention are significantly effective in protective action against external irritation.

Based on the results of the above experimental examples, the compositions containing the ceramide-like compounds of the present invention as an active ingredient will be exemplified in the form of various formulations. It is expected that the composition can increase moisture retention, skin tonicity and recuperation ability, and may protect the skin from the external irritations, thereby defering a skin aging effectively.

<Formulations 32~37>
Skin softners

| Materials | Formulations | | | | | |
|---|---|---|---|---|---|---|
|  | 32 | 33 | 34 | 35 | 36 | 37 |
| Compoud of Example 4 | 0.2 | — | — | — | — | — |
| Compoud of Example 8 | — | 0.2 | — | — | — | — |
| Compoud of Example 27 | — | — | 0.2 | — | — | — |
| Compoud of Example 36 | — | — | — | 0.2 | — | — |
| Compoud of Example 22 | — | — | — | — | 0.2 | — |
| Compoud of Example 45 | — | — | — | — | — | 0.2 |
| Cholesterol | 0.7 | 0.7 | 0.7 | 0.7 | 0.7 | 0.7 |
| Glycerine | 3.0 | 3.0 | 3.0 | 3.0 | 3.0 | 3.0 |
| 1,3-Butyleneglycol | 1.0 | 1.0 | 1.0 | 1.0 | 1.0 | 1.0 |
| Cellulose gum | 0.1 | 0.1 | 0.1 | 0.1 | 0.1 | 0.1 |
| Ethanol | 10.0 | 10.0 | 10.0 | 10.0 | 10.0 | 10.0 |
| POE-16 octyldodecylether | 0.2 | 0.2 | 0.2 | 0.2 | 0.2 | 0.2 |
| Polysorbate-60 | 0.2 | 0.2 | 0.2 | 0.2 | 0.2 | 0.2 |
| Preservative | q.s. | q.s. | q.s. | q.s. | q.s. | q.s. |
| Pigments | q.s. | q.s. | q.s. | q.s. | q.s. | q.s. |
| Perfume | q.s. | q.s. | q.s. | q.s. | q.s. | q.s. |
| Distilled water | to 100 | to 100 | to 100 | to 100 | to 100 | to 100 |

<Formulations 38~43>
Nutrient toilet waters

| Materials | Formulations | | | | | |
|---|---|---|---|---|---|---|
|  | 38 | 39 | 40 | 41 | 42 | 43 |
| Compoud of Example 5 | 1.0 | — | — | — | — | — |
| Compoud of Example 9 | — | 1.0 | — | — | — | — |
| Compoud of Example 28 | — | — | 1.0 | — | — | — |
| Compoud of Example 37 | — | — | — | 1.0 | — | — |
| Compoud of Example 23 | — | — | — | — | 1.0 | — |
| Compoud of Example 46 | — | — | — | — | — | 1.0 |
| Stearic acid | 0.7 | 0.7 | 0.7 | 0.7 | 0.7 | 0.7 |
| Cholesterol | 1.0 | 1.0 | 1.0 | 1.0 | 1.0 | 1.0 |
| Cetostearyl alcohol | 0.7 | 0.7 | 0.7 | 0.7 | 0.7 | 0.7 |
| Polysorbate-60 | 1.5 | 1.5 | 1.5 | 1.5 | 1.5 | 1.5 |
| Sorbitan sesqioleate | 0.5 | 0.5 | 0.5 | 0.5 | 0.5 | 0.5 |
| Liquid paraffin | 5.0 | 5.0 | 5.0 | 5.0 | 5.0 | 5.0 |
| Squalane | 5.0 | 5.0 | 5.0 | 5.0 | 5.0 | 5.0 |
| Glycerine | 5.0 | 5.0 | 5.0 | 5.0 | 5.0 | 5.0 |
| Carboxyvinyl polymer | 0.1 | 0.1 | 0.1 | 0.1 | 0.1 | 0.1 |
| Triethanolamine | 0.12 | 0.12 | 0.12 | 0.12 | 0.12 | 0.12 |
| Preservative | q.s. | q.s. | q.s. | q.s. | q.s. | q.s. |
| Pigments | q.s. | q.s. | q.s. | q.s. | q.s. | q.s. |
| Perfume | q.s. | q.s. | q.s. | q.s. | q.s. | q.s. |
| Distilled water | to 100 | to 100 | to 100 | to 100 | to 100 | to 100 |

<Formulations 44~49>
Nutrient creams

| Materials | Formulations | | | | | |
|---|---|---|---|---|---|---|
|  | 44 | 45 | 46 | 47 | 48 | 49 |
| Compoud of Example 5 | 3.0 | — | — | — | — | — |
| Compoud of Example 9 | — | 3.0 | — | — | — | — |
| Compoud of Example 28 | — | — | 3.0 | — | — | — |
| Compoud of Example 37 | — | — | — | 3.0 | — | — |
| Compoud of Example 24 | — | — | — | — | 3.0 | — |
| Compoud of Example 47 | — | — | — | — | — | 3.0 |
| Cholesterol | 5.0 | 5.0 | 5.0 | 5.0 | 5.0 | 5.0 |
| Cetostearyl alcohol | 3.0 | 3.0 | 3.0 | 3.0 | 3.0 | 3.0 |
| Stearic acid | 2.0 | 2.0 | 2.0 | 2.0 | 2.0 | 2.0 |
| Polysorbate-60 | 1.5 | 1.5 | 1.5 | 1.5 | 1.5 | 1.5 |
| Sorbitan sesqioleate | 0.5 | 0.5 | 0.5 | 0.5 | 0.5 | 0.5 |
| Liquid paraffin | 10.0 | 10.0 | 10.0 | 10.0 | 10.0 | 10.0 |
| Squalane | 10.0 | 10.0 | 10.0 | 10.0 | 10.0 | 10.0 |
| Glycerine | 6.0 | 6.0 | 6.0 | 6.0 | 6.0 | 6.0 |
| Triethanolamine | 0.5 | 0.5 | 0.5 | 0.5 | 0.5 | 0.5 |
| Preservative | q.s. | q.s. | q.s. | q.s. | q.s. | q.s. |
| Pigments | q.s. | q.s. | q.s. | q.s. | q.s. | q.s. |
| Perfume | q.s. | q.s. | q.s. | q.s. | q.s. | q.s. |
| Distilled water | to 100 | to 100 | to 100 | to 100 | to 100 | to 100 |

<Formulations 50~55>
Essences

| Materials | Formulations | | | | | |
|---|---|---|---|---|---|---|
|  | 50 | 51 | 52 | 53 | 54 | 55 |
| Compoud of Example 6 | 1.0 | — | — | — | — | — |
| Compoud of Example 10 | — | 1.0 | — | — | — | — |
| Compoud of Example 28 | — | — | 1.0 | — | — | — |
| Compoud of | — | — | — | 1.0 | — | — |

-continued

| | | | | | | |
|---|---|---|---|---|---|---|
| Example 38 | | | | | | |
| Compoud of Example 25 | — | — | — | — | 1.0 | — |
| Compoud of Example 48 | — | — | — | — | — | 1.0 |
| Myristic acid | 5.0 | 5.0 | 5.0 | 5.0 | 5.0 | 5.0 |
| Cholesterol | 7.0 | 7.0 | 7.0 | 7.0 | 7.0 | 7.0 |
| Cetostearyl alcohol | 1.0 | 1.0 | 1.0 | 1.0 | 1.0 | 1.0 |
| Glycerine | 15.0 | 15.0 | 15.0 | 15.0 | 15.0 | 15.0 |
| 1,3-Butylene-glycol | 4.0 | 4.0 | 4.0 | 4.0 | 4.0 | 4.0 |
| Cellulose gum | 0.1 | 0.1 | 0.1 | 0.1 | 0.1 | 0.1 |
| Hyaruronic acid extracts | 10.0 | 10.0 | 10.0 | 10.0 | 10.0 | 10.0 |
| Carboxyvinyl polymer | 0.12 | 0.12 | 0.12 | 0.12 | 0.12 | 0.12 |
| Triethanol-amine | 0.17 | 0.17 | 0.17 | 0.17 | 0.17 | 0.17 |
| Ethanol | 3.0 | 3.0 | 3.0 | 3.0 | 3.0 | 3.0 |
| Polysorbate-60 | 0.2 | 0.2 | 0.2 | 0.2 | 0.2 | 0.2 |
| POE-25 octyl-dodecylether | 0.2 | 0.2 | 0.2 | 0.2 | 0.2 | 0.2 |
| Preservative | q.s. | q.s. | q.s. | q.s. | q.s. | q.s. |
| Pigments | q.s. | q.s. | q.s. | q.s. | q.s. | q.s. |
| Perfume | q.s. | q.s. | q.s. | q.s. | q.s. | q.s. |
| Distilled water | to 100 | to 100 | to 100 | to 100 | to 100 | to 100 |

<Formulations 56~61>
Cleansin foams

| Materials | Formulations | | | | | |
|---|---|---|---|---|---|---|
| | 56 | 57 | 58 | 59 | 60 | 61 |
| Compoud of Example 5 | 2.0 | — | — | — | — | — |
| Compoud of Example 9 | — | 2.0 | — | — | — | — |
| Compoud of Example 31 | — | — | 2.0 | — | — | — |
| Compoud of Example 37 | — | — | — | 2.0 | — | — |
| Compoud of Example 26 | — | — | — | — | 2.0 | — |
| Compoud of Example 49 | — | — | — | — | — | 2.0 |
| Cholesterol | 5.0 | 5.0 | 5.0 | 5.0 | 5.0 | 5.0 |
| Beeswax | 1.0 | 1.0 | 1.0 | 1.0 | 1.0 | 1.0 |
| Stearic acid | 5.0 | 5.0 | 5.0 | 5.0 | 5.0 | 5.0 |
| Polysorbate-60 | 0.5 | 0.5 | 0.5 | 0.5 | 0.5 | 0.5 |
| Myristic acid | 26.0 | 26.0 | 26.0 | 26.0 | 26.0 | 26.0 |
| KOH | 5.0 | 5.0 | 5.0 | 5.0 | 5.0 | 5.0 |
| Glycerine | 6.0 | 6.0 | 6.0 | 6.0 | 6.0 | 6.0 |
| EDTA-4Na | 0.2 | 0.2 | 0.2 | 0.2 | 0.2 | 0.2 |
| Pigments | q.s. | q.s. | q.s. | q.s. | q.s. | q.s. |
| Perfume | q.s. | q.s. | q.s. | q.s. | q.s. | q.s. |
| Distilled water | to 100 | to 100 | to 100 | to 100 | to 100 | to 100 |

<Formulations 62~67>
Packs

| Materials | Formulations | | | | | |
|---|---|---|---|---|---|---|
| | 62 | 63 | 64 | 65 | 66 | 67 |
| Compoud of Example 5 | 3.0 | — | — | — | — | — |
| Compoud of Example 9 | — | 3.0 | — | — | — | — |
| Compoud of Example 28 | — | — | 3.0 | — | — | — |
| Compoud of Example 37 | — | — | — | 3.0 | — | — |
| Compoud of Example 22 | — | — | — | — | 3.0 | — |
| Compoud of Example 45 | — | — | — | — | — | 3.0 |
| Cholesterol | 0.7 | 0.7 | 0.7 | 0.7 | 0.7 | 0.7 |

-continued

| | | | | | | |
|---|---|---|---|---|---|---|
| Polyvinyl alcohol | 14.0 | 14.0 | 14.0 | 14.0 | 14.0 | 14.0 |
| Cellulose gum | 0.1 | 0.1 | 0.1 | 0.1 | 0.1 | 0.1 |
| Glycerine | 1.0 | 1.0 | 1.0 | 1.0 | 1.0 | 1.0 |
| PEG 4000 | 1.0 | 1.0 | 1.0 | 1.0 | 1.0 | 1.0 |
| POE-16 octyl-dodecylether | 0.4 | 0.4 | 0.4 | 0.4 | 0.4 | 0.4 |
| Ethanol | 6.0 | 6.0 | 6.0 | 6.0 | 6.0 | 6.0 |
| Preservative | q.s. | q.s. | q.s. | q.s. | q.s. | q.s. |
| Pigments | q.s. | q.s. | q.s. | q.s. | q.s. | q.s. |
| Perfume | q.s. | q.s. | q.s. | q.s. | q.s. | q.s. |
| Distilled water | to 100 | to 100 | to 100 | to 100 | to 100 | to 100 |

What is claimed is:

1. A compound represented by the formula (I):

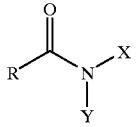

wherein,

R represents a $C_{9\sim31}$ linear or branched, saturated or unsaturated, hydroxylated or non-hydroxylated alkyl group, or RCO is 2-dodecen-1-yl succinoyl;

and A) when Y represents a $C_{10\sim32}$ linear or branched, saturated or unsaturated, hydroxylated or non-hydroxylated alkyl group, X represents a group having the structure:

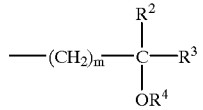

wherein, m is 1;

$R^2$ and $R^3$ each represents H; and $R^4$ represents $-CH_2CH_2OA^1$, wherein $A^1$ represents H or any one of the following structures:

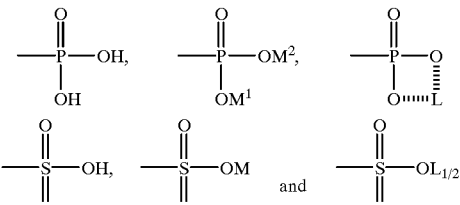

wherein,

M, $M^1$ and $M^2$ each represents independently an alkali metal or an organic base containing nitrogen; and L represents an alkaline earth metal, or B) when Y represents a group having the structure:

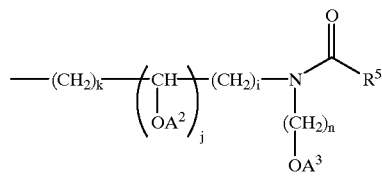

wherein, n is an integer from 1 to 3, inclusive;

k and i are independently an integer from 1 to 3, inclusive;

j is 0 or 1;

$R^5$ represents a $C_{9-31}$ linear or branched-chain, saturated or unsaturated, hydroxylated or non-hydroxylated alkyl group;

$A^2$ and $A^3$ have the same meanings as $A^1$, independently with the proviso that $A^1$ is not H, when R is a $C_{9-31}$ linear alkyl group Y is a $C_{10-32}$ linear alkyl group, or when j=0 and each of R and $R^5$ independently is a $C_{9-31}$ linear alkyl group; and X represents a group having the structure:

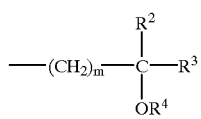

wherein, m is 1;

$R^2$ and $R^3$ each represent H; and $R^4$ represents $A^1$ or $-CH_2CH_2OA^1$, wherein $A^1$ represents H or any one of the structures:

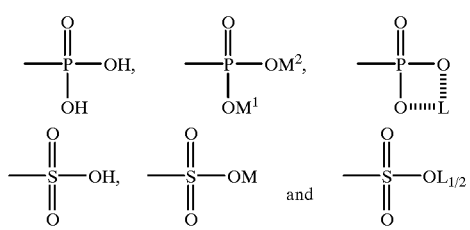

wherein,

M, $M^1$ and $M^2$ each represents independently an alkali metal or an organic base containing nitrogen, and L represents an alkaline earth metal.

2. The compound (I) according to claim 1, which is represented by the formula (I-1):

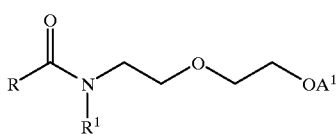

wherein, R represents a $C_{9-31}$ linear or branched, saturated or unsaturated, hydroxylated or non-hydroxylated alkyl group, and $R^1$ represents a $C_{10-32}$ linear or branched, saturated or unsaturated, hydroxylated or non-hydroxylated alkyl group, and $A^1$ has the same meaning as defined in said formula (I) with the proviso that $A^1$ is not H, when R is a $C_{9-31}$ linear alkyl group and Y is a $C_{10-32}$ linear alkyl group.

3. The compound (I) according to claim 2, wherein $A^1$ is H.

4. The compound (I) according to claim 2, wherein $A^1$ has the same meaning as defined in said formula (I), except that $A^1$ is H.

5. The compound (I) according to claim 1, which is represented by the formula (I-2):

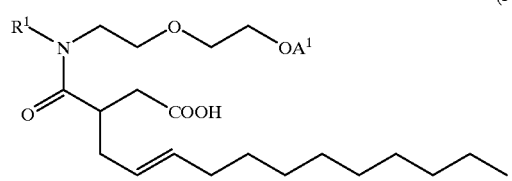

wherein, $R^1$ represents a $C_{10-32}$ linear or branched, saturated or unsaturated, hydroxylated or non-hydroxylated alkyl group and $A^1$ has the same meaning as defined in said formula (I).

6. The compound (I) according to claim 5, wherein $A^1$ is H.

7. The compound (I) according to claim 5, wherein $A^1$ has the same meaning as defined in said formula (I), except that $A^1$ is H.

8. The compound (I) according to claim 1, which is represented by the formula (I-3):

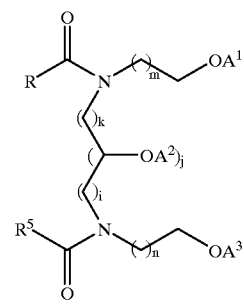

wherein, both R and $R^5$, which may be the same or different, each represents a $C_{9-31}$ linear or branched, saturated or unsaturated, hydroxylated or non-hydroxylated alkyl group, and $A^1$, $A^2$, $A^3$, i, j, k, m and n have the same meanings as defined in said formula (I) respectively with the proviso that $A^1$ is not H, when j=0 and both $R^5$ are $C_{9-31}$ linear alkyl groups, independently.

9. The compound (I) according to claim 8, wherein $A^1$, $A^2$ and $A^3$ are all H.

10. A method for preparing said compound (I-1) of claim 2, which comprises the steps of:

(1) reacting an aliphatic amine with 2-(2-chloroethoxy) ethanol in ethanol, to produce a secondary amine derivative represented by the formula (II):

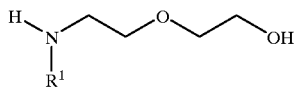

wherein $R^1$ has the same meaning as defined in said formula (I-1);

(2) reacting said secondary amine derivative of said step (1) with $C_{10\sim32}$ fatty ester in the presence of an alkali catalyst, to produce an amide compound; and (3) dissolving said amide compound of said step (2) in a first organic solvent, and filtering off precipitates thus formed, and then recrystallizing a product from a second organic solvent.

11. The method according to claim 10, wherein the reaction of said step (1) is carried out at a temperature of 50~90° C., and the reaction of said step (2) is carried out at a temperature of 110~150° C.

12. The method according to claim 10, which further comprises the steps of (4) phosphorylating or sulfating said amide compound obtained in said step (3); and then (5) neutralizing the product of the step (4) with alkali or base.

13. The method according to claim 12, wherein a phosphorylating reagent employed in said step (4) is selected from the group consisting of phosphorus oxychloride and phosphoric anhydride.

14. The method according to claim 12, wherein a sulfating reagent employed in said step (4) is selected from the group consisting of chlorosulfonic acid and sulfur trioxide.

15. The method according to claim 12, wherein a neutralizing agent employed in said step (5) is selected from the group consisting of alkali metal oxides; alkaline earth metal oxides; basic amino acids; ammonia; amines; cationic polymers; and cationic surfactants.

16. A method for preparing said compound (I-2) of claim 5, which comprises steps of:

(1) reacting an aliphatic amine with 2-(2-chloroethoxy) ethanol in ethanol, to produce a secondary amine derivative represented by the formula (II):

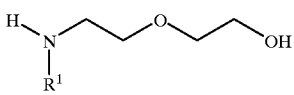

wherein, $R^1$ has the same meaning as defined in said formula (I-2);

(2) reacting said secondary amine derivative of said step (1) with 2-dodecen-1-yl succinic anhydride, to produce an amide compound; and (3) removing solvent by evaporation, and then subjecting a residue to a column chromatography.

17. The method according to claim 16, wherein the reaction of said step (1) is carried out at a temperature of 50~90° C., and the reaction of said step (2) is carried out at a temperature of 20~50° C.

18. The method according to claim 17, which further comprises the steps of (4) phosphorylating or sulfating said amide compound obtained in said step (3); and then (5) neutralizing the product of the step (4) with alkali or base.

19. A method for preparing said compound (I-3) of claim 8, which comprises the steps of:

(1) reacting a primary amino alcohol, with a dihalo compound or a monohalo epoxy compound in ethanol, to produce a secondary amino alcohol derivative represented by the formula (IV):

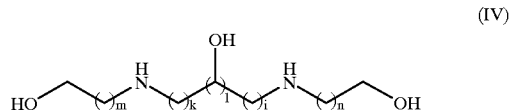

wherein i, j, k, m and n have the same meanings as defined in said formula (I-3), respectively;

(2) reacting said secondary amino alcohol derivative of said step (1) with a $C_{10\sim32}$ fatty acid chloride in the presence of an alkali or organic base as a catalyst, to produce a diamide compound; and (3) dissolving said diamide compound of said step (2) in an organic solvent, and filtering off precipitates, and then recrystallizing a product from an organic solvent.

20. The method according to claim 19, wherein said dihalo compound of said step (1) is selected from the group consisting of 1,3-dichloro-2-propanol, 1,3-dibromo-1-propanol and $C_{2\sim6}$ alkyl dihalide; and said monohalo epoxy compound of said step (1) is selected from the group consisting of epibromohydrin, epibromohydrin, 3,4-epoxy-1-chlorobutane, 3,4-epoxy-1-bromobutane, 4,5-epoxy-1-chloropentane and 4,5-epoxy-1-bromopentane.

21. The method according to claim 19, wherein the reaction of said step (2) is carried out at a temperature of 10~30° C.

22. The method according to claim 19, which further comprises the steps of (4) phosphorylating or sulfating said diamide compound obtained in said step (3); and then (5) neutralizing the product of the step (4) with alkali or base.

23. The method according to claim 22, wherein a phosphorylating reagent employed in said step (4) is selected from the group consisting of phosphorus oxychloride and phosphoric anhydride.

24. The method according to claim 22, wherein a sulfating reagent employed in said step (4) is selected from the group consisting of chlorosulfonic acid and sulfur trioxide.

25. The method according to claim 22, wherein a neutralizing, agent employed in said step (5) is selected from the group consisting of alkali metal oxides; alkaline earth metal oxides; basic amino acids; ammonia; amines; cationic polymers; and cationic surfactants.

26. A cosmetic composition containing said compound (I) claimed in claim 1.

27. The cosmetic composition according to claim 26, wherein said compound is contained in an amount of 0.001~20% by weight.

28. The method according to claim 10, wherein the first organic solvent is selected from the group consisting of chloroform and dichloroethane.

29. The method according to claim 10, wherein the second organic solvent is selected from the group consisting of hexane and acetone.

30. The method according to claim 15, wherein the alkali metal oxides are selected from the group consisting of sodium hydroxide and potassium hydroxide.

31. The method according to claim 15, wherein the alkaline earth metal oxides are selected from the group consisting of calcium hydroxide, magnesium hydroxide, calcium oxide, and magnesium oxide.

32. The method according to claim 15, wherein the basic amino acids are selected from the group consisting of lysine, arginine, and histidine.

33. The method according to claim 15, wherein the amine is triethanol amine.

34. The method according to claim 15, wherein the cationic polymers are selected from the group consisting of polyquaternium-4, polyquaternium-6, polyquaternium-7, polyquaternium-10, polyquaternium-11, and polyquaternium-16.

35. The method according to claim 15, wherein the cationic surfactants are selected from the group consisting of lauryldimethylbenzyl ammonium chloride and stearyldimethylbenzyl ammonium chloride.

36. The method according to claim 19, wherein the primary amino alcohol is selected from the group consisting of ethanolamine, 3-amino-1-propanol, and 4-aminobutanol.

37. The method according to claim 19, wherein the organic solvent is selected from the group consisting of acetone, chloroform/acetone, or chloroform/hexane.

38. The method according to claim 20, wherein the $C_{2-6}$ alkyl dihalide is selected from the group consisting of 1,2-dibromoethane and 1,2-dichloroethane.

39. The method according to claim 25, wherein the alkali metal oxides are selected from the group consisting of sodium hydroxide and potassium hydroxide.

40. The method according to claim 25, wherein the alkaline earth metal oxides are selected from the group consisting of calcium hydroxide, magnesium hydroxide, calcium oxide, and magnesium oxide.

41. The method according to claim 25, wherein the basic amino acids are selected from the group consisting of lysine, arginine, and histidine.

42. The method according to claim 25, wherein the amine is triethanol amine.

43. The method according to claim 25, wherein the cationic polymers are selected from the group consisting of polyquaternium-4, polyquaternium-6, polyquaternium-7, polyquaternium-10, polyquaternium-11, and polyquaternium-16.

44. The method according to claim 25, wherein the cationic surfactants are selected from the group consisting of lauryldimethylbenzyl ammonium chloride and stearyldimethylbenzyl ammonium chloride.

* * * * *